United States Patent [19]

Sohda et al.

[11] Patent Number: 5,436,247
[45] Date of Patent: Jul. 25, 1995

[54] QUINOLINE OR QUINAZOLINE DERIVATIVES, THEIR PRODUCTION AND USE

[75] Inventors: Takashi Sohda, Takatsuki; Haruhiko Makino, Inagawa; Atsuo Baba, Ashiya, all of Japan

[73] Assignee: Takeda Chemical Industries, Osaka, Japan

[21] Appl. No.: 186,638

[22] Filed: Jan. 26, 1994

[30] Foreign Application Priority Data

Jan. 28, 1993 [JP] Japan ................................. 5-012628
Aug. 20, 1993 [JP] Japan ................................. 5-206128

[51] Int. Cl.⁶ .................. A61K 31/47; A61K 31/505; C07D 239/74; C07D 215/60
[52] U.S. Cl. .................. 514/259; 514/314; 544/284; 546/173
[58] Field of Search .................. 544/284; 546/173; 514/259, 314

[56] References Cited

FOREIGN PATENT DOCUMENTS 0125756 11/1984 European Pat. Off. .
0371564 6/1990 European Pat. Off. .

OTHER PUBLICATIONS

IL FARMACO, vol. 47, No. 2, Feb. 1992, Italy, pp. 191–202.
Journal of Medicinal Chemistry, vol. 28, No. 10, Oct. 1985, Washington US, pp. 1394–1398.
IL FARMACO, vol. 44, No. 6, Jun. 1989, Italy, pp. 555–563.
Synthesis, No. 9, 1979, Stuttgart DE, pp. 718–719.
European Search Report, EP 9410114.7 1994.
Synthesis, pp. 718–719, Gatta et al., Sep. 1979.
IL FARMACO, 44 (6), pp. 555–563, 1989, M. Anzini et al.

*Primary Examiner*—Mukund J. Shah
*Assistant Examiner*—Matthew V. Grumbling
*Attorney, Agent, or Firm*—Foley & Lardner

[57] ABSTRACT

A compound represented by the general formula:

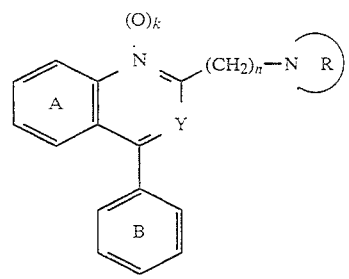

wherein Y represents a nitrogen atom or C—G (G represents a carboxyl group which may be esterified); ring R is a nitrogen-containing unsaturated heterocyclic group which may be substituted or unsubstituted; each of rings A and B may have a substituent; n represents an integer from 1 to 4; k represents the integer 0 or 1, or a salt thereof, which serves well as an anti-inflammatory agent, particularly a therapeutic agent for arthritis.

19 Claims, No Drawings

QUINOLINE OR QUINAZOLINE DERIVATIVES, THEIR PRODUCTION AND USE

FIELD OF THE INVENTION

The present invention relates to a new quinoline or quinazoline derivative or a salt thereof which serves well as an anti-inflammatory agent, particularly a therapeutic agent for arthritis. Additionally, these compouns and compositions can be used in the diagnosis of such disease states.

BACKGROUND OF THE INVENTION

Arthritis, an inflammatory disease of the joint, occurs in various forms such as rheumatoid arthritis and related diseases with joint inflammation.

Rheumatoid arthritis, also called chronic rheumatism, in particular, is a chronic multiple arthritis characterized by inflammatory changes in the synovial membrane of the articular capsule inner layer. Arthritic diseases like rheumatoid arthritis are progressive and cause joint disorders such as deformation and acampsia, often resulting in severe physical disorder due to lack of effective treatment and subsequent deterioration.

Traditionally, these forms of arthritis have been chemotherapeutically treated with various agents, including steroids such as cortisone and other adrenocortical hormones, non-steroidal anti-inflammatory agents such as aspirin, piroxicam and indomethacin, gold agents such as aurothiomalate, antirheumatic agents such as chloroquine preparations and D-penicillamine, antigout agents such as colchicine, and immunosuppressors such as cyclophosphamide, azathioprine, methotrexate and levamisole.

However, these drugs have drawbacks such as severe adverse reactions, adverse reactions hampering the drug's long-term use, lack of sufficient efficacy and a failure to be effective against already-occurring arthritis.

Accordingly, there is need for the development of a drug which exhibits excellent prophylactic/therapeutic action on arthritis, with low toxicity in clinical situations.

Traditionally, various compounds have been synthesized as quinoline or quinazoline derivatives. Known compounds having an aminomethyl group at the 2-position of a 4-phenylquinoline or 4-phenylquinazoline skeleton include the 2-dimethylaminomethyl derivative and 2-morpholinomethyl derivative described in Synthesis, Vol. 9, p. 718 (1979), and the 2-alkylaminomethylquinoline derivative described in the Farmaco, Vol. 44, 555 (1989). However, there is no disclosure of any compound wherein the 2-position of a 4-phenylquinoline or 4-phenylquinazoline skeleton is bound to a nitrogen atom of a nitrogen-containing unsaturated heterocyclic ring via an alkylene group as in the present invention.

OBJECTS OF THE INVENTION

One object of the invention is to provide a novel quinoline or quinazoline derivatives useful as an anti-inflammatory agent.

Another object of the invention is to provide method for producing the above quinoline or quinazoline derivatives.

Further, another object of the present invention is to provide a novel anti-inflammatory agent containing a quinoline or quinazoline derivative.

These object as well as other objects and advantages of the present invention will become apparent to those skilled in the art from the following description.

SUMMARY OF THE INVENTION

The present inventors found that a compound wherein the 2-position of a 4-phenylquinoline or 4-phenylquinazoline skeleton is bound to a nitrogen atom of a nitrogen-containing unsaturated heterocyclic ring via an alkylene group exhibits anti-arthritic action and serves well as a joint destruction suppressor. The inventors made investigations based on this finding, and developed the present invention.

Accordingly, the present invention relates to:

(1) a compound represented by general formula (I):

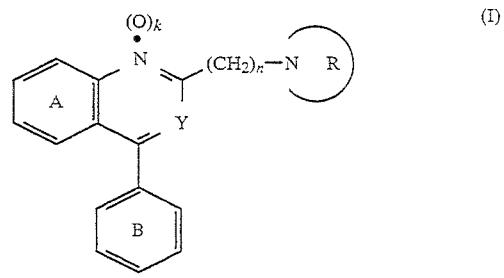

wherein Y represents a nitrogen atom or C—G (G represents a carboxyl group which may be esterified); ring R is a nitrogen-containing unsaturated heterocyclic group which may be substituted or unsubstituted; each of rings A and B may have substituents; n represents an integer from 1 to 4; k represents the integer 0 or 1, or a salt thereof;

(2) a method of producing a compound represented by general formula (I):

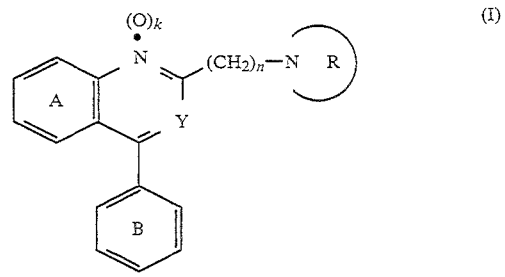

wherein Y represents a nitrogen atom or C—G (G represents a carboxyl group which may be esterified); rings A and B may have substituents; ring R represents a nitrogen-containing unsaturated heterocyclic group which may be substituted or unsubstituted; n represents an integer from 1 to 4; k represents the integer 0 or 1, or a salt thereof; by reacting a compound represented by general formula (II):

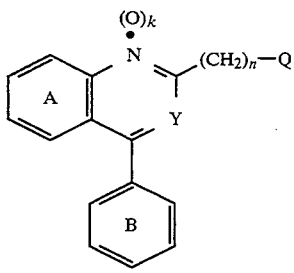

(II)

wherein Q represents a leaving group; the other symbols have the same definitions as above, with a compound represented by general formula (III):

(III)

wherein ring R has the same definition as above, and (3) an anti-inflammatory agent containing a compound represented by general formula (I):

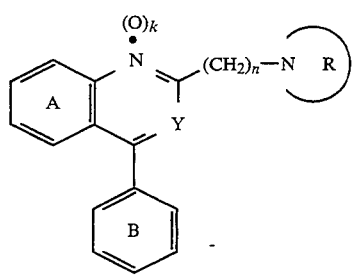

(I)

wherein Y represents a nitrogen atom or C—G (G represents a carboxyl group which may be esterified); ring R is a nitrogen-containing unsaturated heterocyclic group which may be substituted or unsubstituted; each of rings A and B may have substituents; n represents an integer from 1 to 4; k represents the integer 0 or 1, or a salt thereof.

The above general formulas and various definitions included in the scope of the present invention are hereinafter described in detail with typical examples thereof.

DETAILED DESCRIPTION OF THE INVENTION

With respect to general formulas (I) and (III), the nitrogen-containing unsaturated heterocyclic group for ring R, which may be substituted or unsubstituted, is exemplified by unsaturated heterocyclic rings containing 1 or more nitrogen atoms, preferably 1 to 4 nitrogen atoms as ring component atoms. Preferable unsaturated heterocyclic groups include 5-membered nitrogen-containing unsaturated heterocyclic groups such as imidazol-1-yl, pyrazol-1-yl, 1,2,4-triazol-1-yl, 1,2,4-triazol-4-yl, 1,2,3-triazol-1-yl, 1,2,3-triazol-2-yl, pyrrol-1-yl and tetrazol-1-yl, 2-pyrrolin-1-yl, 3-pyrrolin-1-yl, 2-imidazolin-1-yl, 2-pyrazolin-1-yl, 3-pyrazolin-1-yl, each of which may form a condensed ring (e.g., benzimidazol-1-yl, indol-1-yl, 1H-indazol-1-yl, benzotriazol-1-yl, benzotriazol-2-yl, isoindol-2-yl, 7-purinyl, 1H-pyrrolo[1,2-b][1,2,4]triazol-1-yl, 1,8-dihydroimidazo[1,2-a]pyridin- 1-yl, 1,8a-dihydro[1,2,4]-triazolo[1,5a]pyridin-1-yl, 3,3a-dihydro[1,2,4]-triazolo[1,5-a]pyrimidin-3-yl, 1,8a-dihydroimidazo[1,2-a]pyrimidin-1-yl, 1H-pyrazolo[4,3-d]oxazol-1-yl, 4H-imidazo[4,5-d]thiazol-4-yl etc.) and also include 6-membered nitrogen-containg unsaturated heterocyclic groups such as 1,4-dihydropyridin-1-yl, 1,2-dihydropyridin-1-yl. These unsaturated heterocyclic groups may have 1 to 3 substituents at any positions thereon. These substituents are exemplified by aliphatic chain hydrocarbon groups, alicyclic hydrocarbon groups, aryl groups, aromatic heterocyclic groups, non-aromatic heterocyclic groups, halogen atoms, nitro groups, amino groups which may be substituted or unsubstituted, acyl groups which may be substituted or unsubstituted, hydroxyl groups which may be substituted or unsubstituted, thiol groups which may be substituted or unsubstituted and carboxyl groups which may be esterified.

Such aliphatic chain hydrocarbon groups include linear or branched aliphatic hydrocarbon groups such as alkyl groups, preferably those having 1 to 10 carbon atoms, alkenyl groups, preferably those having 2 to 10 carbon atoms, and alkynyl groups.

Preferable alkyl groups include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl and decyl.

Preferable alkenyl groups include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

Preferable alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

Such alicyclic hydrocarbon groups include saturated or unsaturated alicyclic hydrocarbons such as cycloalkyl groups, cycloalkenyl groups and cycloalkadienyl groups.

Preferable cycloalkyl groups include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl.

Preferable cycloalkenyl groups include 2-cyclopenten-1-yl, 3-cyclopenten-1-yl, 2-cyclohexen-1-yl and 3-cyclohexen-1-yl.

Preferable cycloalkadienyl groups include 2,4-cyclopentadien-1-yl, 2,4-cyclohexadien-1-yl and 2,5-cyclohexadien- 1-yl.

Such aryl groups are monocyclic or condensed polycyclic aromatic hydrocarbon groups, preferably phenyl, naphthyl, anthryl, phenanthryl, acenaphthylenyl and others, with greater preference given to phenyl, 1-naphthyl, 2-naphthyl and others.

Preferable aromatic heterocyclic groups include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxthinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl.

Preferable non-aromatic heterocyclic groups include oxylanyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl.

Such halogen atoms include atoms of fluorine, chlorine, bromine and iodine, with preference given to atoms of fluorine and chlorine.

Such amino groups include amino groups (—NH$_2$ groups) substituted with 1 or 2 alkyl groups having 1 to 10 carbon atoms, alkenyl groups having 1 to 10 carbon atoms, aromatic groups or an acyl group having one to ten carbon atoms (e.g., methylamino, dimethylamino, ethylamino, diethylamino, dibutylamino, diallylamino, cyclohexylamino, phenylamino, N-methyl-N-phenylamino, acetylamino, propionylamino, benzoylamino etc.).

Such acyl groups include formyl and groups resulting from binding of an alkyl group having 1 to 10 carbon atoms, alkenyl group having 1 to 10 carbon atoms or aromatic group and a carbonyl group (e.g., acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl).

Such hydroxyl groups include the hydroxyl group and hydroxyl groups having an appropriate substituent, particularly a substituent for use as a hydroxyl group protecting group, such as alkoxy, alkenyloxy, aralkyloxy and acyloxy, as well as aryloxy. Said alkoxy is preferably an alkoxy having 1 to 10 carbon atoms (e.g., methoxy, ethoxy, propoxy, isopropoxy, butoxy, isobutoxy, sec-butoxy, tert-butoxy, pentoxy, isopentoxy, neopentoxy, hexyloxy, heptyloxy, nonyloxy, cyclobutoxy, cyclopentoxy, cyclohexyloxy). Said alkenyloxy is exemplified by alkenyloxys having 1 to 10 carbon atoms such as allyloxy, crotyloxy, 2-pentenyloxy, 3-hexenyloxy, 2-cyclopentenylmethoxy and 2-cyclohexenylmethoxy. Said aralkyloxy is exemplified by phenyl-C$_{1-4}$ alkyloxys (e.g., benzyloxy, phenethyloxy). Said acyloxy is preferably an alkanoyloxy having 2 to 4 carbon atoms (e.g., acetyloxy, propionyloxy, n-butyryloxy, isobutyryloxy). Said aryloxy is exemplified by phenoxy and 4-chlorophenoxy.

Such thiol groups include the thiol group and thiol groups having an appropriate substituent, particularly a substituent for use as a thiol group protecting group, such as alkylthio, aralkylthio and acylthio. Said alkylthio is preferably an alkylthio having 1 to 10 carbon atoms (e.g., methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio). Said aralkylthio is exemplified by phenyl-C$_{1-4}$ alkylthios (e.g., benzylthio, phenethylthio). Said acylthio is preferably an alkanoylthio having 2 to 4 carbon atoms (e.g., acetylthio, propionylthio, n-butyrylthio, isobutyrylthio).

Such carboxyl groups include carboxyl groups, alkyloxycarbonyl groups and aralkyloxycarbonyl groups.

The alkyl group in said alkyloxycarbonyl groups is exemplified by alkyl groups having 1 to 6 carbon atoms, such as methyl, ethyl, propyl, isopropyl, butyl, isobutyl, sec-butyl and tert-butyl.

The aralkyl group in said aralkyloxycarbonyl groups is an alkyl group having an aryl group as a substituent (arylalkyl group). Said aryl group is exemplified by phenyl and naphthyl, each of which may have the same substituents as specified for the aryl group on ring R above. Said alkyl group is preferably a lower alkyl group having 1 to 6 carbon atoms. Preferable aralkyl groups include benzyl, phenethyl, 3-phenylpropyl, (1-naphthyl)methyl and (2-naphthyl)methyl, with preference given to benzyl, phenetyl and others.

The above-described aliphatic chain hydrocarbon groups, alicyclic hydrocarbon groups, aryl groups, heterocyclic groups and others may each have 1 or more, preferably 1 to 3, appropriate substituents. These substituents include lower alkyl groups, lower alkenyl groups, lower alkynyl groups, cycloalkyl groups, aryl groups, aromatic heterocyclic groups, non-aromatic heterocyclic groups, aralkyl groups, amino groups, N-mono-substituted amino groups, N,N-di-substituted amino groups, amidino groups, acyl groups, carbamoyl groups, N-mono-substituted carbamoyl groups, N,N-di-substituted carbamoyl groups, sulfamoyl groups, N-mono-substituted sulfamoyl groups, N,N-di-substituted sulfamoyl groups, carboxyl groups, lower alkoxycarbonyl groups, hydroxyl groups, lower alkoxy groups, lower alkenyloxy groups, cycloalkyloxy groups, aralkyloxy groups, aryloxy groups, mercapto groups, lower alkylthio groups, aralkylthio groups, arylthio groups, sulfo groups, cyano groups, azide groups, nitro groups, nitroso groups and halogens.

With respect to general formulas (I) and (II), provided that Y is a quinoline derivative represented by C—G, the carboxyl group for G, which may be esterified, is exemplified by the carboxyl group, alkyloxycarbonyl group and aralkyloxycarbonyl group. The alkyl group in said alkyloxycarbonyl group is exemplified by alkyl groups having 1 to 6 carbon atoms, such as methyl, ethyl, propyl, isopropyl, butyl, isobutyl, sec-butyl and tert-butyl.

The aralkyl group in said aralkyloxycarbonyl group is an alkyl group having an aryl group as a substituent (arylalkyl group). Said aryl group is exemplified by phenyl and naphthyl, which may have the same substituents as those contained in the aryl group for ring R above. Said alkyl group is preferably a lower alkyl group having 1 to 6 carbon atoms. Such preferable aralkyl groups include benzyl, phenethyl, 3-phenylpropyl, (1-naphthyl)methyl and (2-naphthyl)methyl, with preference given to benzyl, phenetyl and others.

With respect to general formula (II), the leaving group for Q is exemplified by halogen atoms, preferably atoms of chlorine, bromine and iodine, hydroxyl groups esterificated by organic sulfonic acid residues (e.g., p-toluenesulfonyloxy group, methanesulfonyloxy group) and organic phosphoric acid residues such as the diphenylphosphoryloxy group, dibenzylphosphoryloxy group and dimethylphosphoryloxy group.

With respect to general formulas (I) and (II), rings A and B may have substituents. These substituents are exemplified by halogen atoms, nitro groups, alkyl groups which may be substituted for, hydroxyl groups which may be substituted or unsubstituted, thiol groups which may be substituted for, amino groups which may be substituted or unsubstituted, acyl groups which may be substituted or unsubstituted, carboxyl groups which may be esterified and aromatic ring groups which may be substituted or unsubstituted. Such substituent halogen atoms include atoms of fluorine, chlorine, bromine and iodine, with preference given to atoms of fluorine and chlorine. The alkyl group which may be substituted for may be any one having 1 to 10 carbon atoms, whether linear, branched or cyclic, exemplified by methyl, ethyl, propyl, isopropyl, butyl, isobutyl, sec-butyl, tert-butyl, pentyl, isopentyl, neopentyl, hexyl, heptyl, octyl, nonyl, decyl, cyclopropyl, cyclobutyl, cyclopentyl, cyclohexyl and cycloheptyl. The hydroxyl group which may be substituted or unsubstituted is exemplified by the hydroxyl group and hydroxyl groups having an appropriate substituent, particularly a substituent used as a hydroxyl group protecting group, such as alkoxy, alkenyloxy, aralkyloxy and acyloxy, as well as aryloxy. Said alkoxy is preferably an alkoxy having 1 to 10 carbon atoms (e.g., methoxy, ethoxy, propoxy, isopropoxy, butoxy, isobutoxy, sec-butoxy, tert-butoxy, pentoxy, isopentoxy, neopentoxy, hexyloxy, heptyloxy, nonyloxy, cyclobutoxy, cyclopentoxy, cyclohexyloxy). Said alkenyloxy is exemplified by alkenyloxys having 1 to 10 carbon atoms such as allyloxy, crotyloxy, 2-pentenyloxy, 3-hexenyloxy, 2-cyclopentenylmethoxy and 2-cyclohexenylmethoxy. The aralkyloxy is exemplified by phenyl-$C_{1-4}$ alkyloxys (e.g., benzyloxy, phenethyloxy). Said acyloxy is preferably an alkanoyloxy having 2 to 4 carbon atoms (e.g., acetyloxy, propionyloxy, n-butyryloxy, isobutyryloxy). Said aryloxy is exemplified by phenoxy and 4-chlorophenoxy. The thiol group which may be substituted or unsubstituted is exemplified by the thiol group and thiol groups having an appropriate substituent, particularly a substituent used as a thiol group protecting group, such as alkylthio, aralkylthio and acylthio. Said alkylthio is preferably an alkylthio having 1 to 10 carbon atoms (e.g., methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio). Said aralkylthio is exemplified by phenyl-$C_{1-4}$ alkylthios (e.g., benzylthio, phenethylthio). Said acylthio is preferably an alkanoylthio having 2 to 4 carbon atoms (e.g., acetylthio, propionylthio, n-butyrylthio, isobutyrylthio). The amino group which may be substituted or unsubstituted is exemplified by amino groups (—$NH_2$ groups) substituted for by 1 or 2 of alkyl groups having 1 to 10 carbon atoms, alkenyl groups having 1 to 10 carbon atoms, aromatic groups and an acyl group having one to ten carbon atoms (e.g., methylamino, dimethylamino, ethylamino, diethylamino, dibutylamino, diallylamino, cyclohexylamino, phenylamino, N-methyl-N-phenylamino, acetylamino, propionylamino, benzoylamino etc.). The acyl group which may be substituted or unsubstituted is exemplified by formyls and groups resulting from binding of an alkyl group having 1 to 10 carbon atoms, alkenyl group having 1 to 10 carbon atoms or aromatic group and a carbonyl group (e.g., acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl). The carboxyl group which may be esterified is exemplified by carboxyl groups, alkyloxycarbonyl groups and aralkylcarbonyl groups. The alkyl group in said alkyloxycarbonyl group is exemplified by alkyl groups having 1 to 6 carbon atoms such as methyl, ethyl, propyl, isopropyl, butyl, isobutyl, sec-butyl and tert-butyl.

The aralkyl group in said aralkyloxycarbonyl group is an alkyl group having an aryl group as a substituent (arylalkyl group). The aryl group is exemplified by phenyl and naphthyl, which may have the same substituents as those contained in the aryl group for ring R above. Said alkyl group is preferably a lower alkyl group having 1 to 6 carbon atoms. Preferable aralkyl groups include benzyl, phenetyl, 3-phenylpropyl, (1-naphthyl)methyl and (2-naphthyl)methyl, with preference given to benzyl, phenetyl and others. The aromatic ring group which may be substituted for is exemplified by aromatic heterocyclic residues such as pyridyl, furyl, thienyl, imidazolyl and thiazolyl, as well as $C_{6-14}$ aromatic hydrocarbon residues such as phenyl, naphthyl and anthryl.

Such substituents for rings A and B may be present at any positions of each ring, and 1 to 4 substituents, whether identical or not, may be present on each ring. Provided that substituents on ring A or B are mutually adjacent, they may bind together to form a ring represented by —$(CH_2)_m$— (m represents an integer from 3 to 5) or —O—$(CH_2)_l$—O—(l represents an integer from 1 to 3), ring which may be a 5- to 7-membered ring formed in cooperation with carbon atoms on the benzene ring.

The salt of compound (I), the desired compound of the present invention, is preferably a pharmaceutically acceptable salt, exemplified by salts with inorganic bases, salts with organic bases, salts with inorganic acids, salts with organic acids and salts with basic or acidic amino acids. Preferable salts with inorganic base include alkali metal salts such as sodium salt and potassium salt, alkaline earth metal salts such as calcium salt and magnesium salt, aluminum salt and ammonium salt. Preferable salts with organic base include salts with trimethylamine, triethylamine, pyridine, picoline, ethanolamine, diethanolamine, triethanolamine, dicyclohexylamine and N,N'-dibenzylethylenediamine. Preferable salts with inorganic acid include salts with hydrochloric acid, hydrobromic acid, nitric acid, sulfuric acid and phosphoric acid. Preferable salts with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Preferable salts with basic amino acid include salts with arginine, lysine and ornithine. Preferable salts with acidic amino acid include salts with aspartic acid and glutamic acid.

Compound (I), the desired compound of the present invention, can be administered orally or non-orally, along with a pharmaceutically acceptable carrier, in the form of solid preparations such as tablets, capsules, granules and powders, or liquid preparations such as syrups and injectable preparations.

Pharmaceutically acceptable carriers are various organic or inorganic carrier substances in common use as pharmaceutical materials, including excipients, lubricants, binders and disintegrating agents for solid preparations, and solvents, dissolution aids, suspending agents, isotonizing agents, buffers and soothing agents for liquid preparations. Other pharmaceutical additives such as preservatives, antioxidants, coloring agents and sweetening agents may be used as necessary. Preferable excipients include lactose, sucrose, D-mannitol, starch, crystalline cellulose and light silicic anhydride. Preferable lubricants include magnesium stearate, calcium stearate, talc and colloidal silica. Preferable binders include crystalline cellulose, sucrose, D-mannitol, dextrin, hydroxypropyl cellulose, hydroxypropylmethyl cellulose and polyvinylpyrrolidone. Preferable disintegrating agents include starch, carboxymethyl cellulose, carboxymethyl cellulose calcium, crosscalmellose sodium and carboxymethyl starch sodium. Preferable solvents include water for injection, alcohol, propylene glycol, macrogol, sesame oil and corn oil. Preferable dissolution aids include polyethylene glycol, propylene glycol, D-mannitol, benzyl benzoate, ethanol, trisaminomethane, cholesterol, triethanolamine, sodium carbonate and sodium citrate. Preferable suspending agents include surfactants such as stearyltriethanolamine, sodium lauryl sulfate, laurylaminopropionic acid, lecithin, benzalkonium chloride, benzethonium chloride and monostearic glycerol, and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include sodium chloride, glycerol and D-mannitol. Preferable buffers include phosphate, acetate, carbonate or citrate buffer solutions. Preferable soothing agents include benzyl alcohol. Preferable preservatives include p-oxybenzoates, chlorobutanol, benzyl alcohol, phenethyl alcohol, dehydroacetic acid and sorbic acid. Preferable antioxidants include sulfites and ascorbic acid.

Compound (I) can, for example, be produced as follows:

Method A

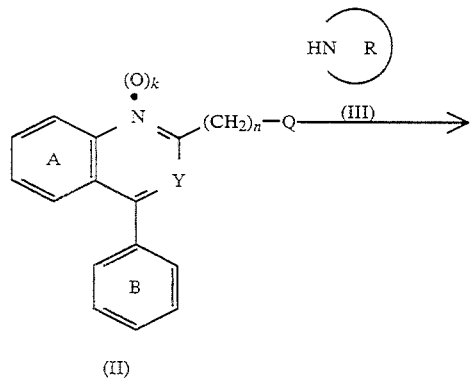

(II)

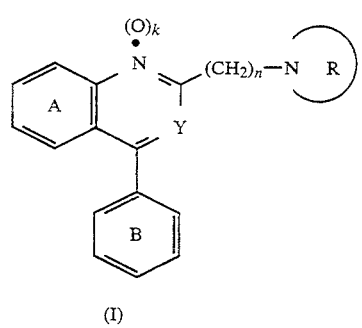

(I)

wherein the symbols have the same definitions as above.

In this method, compound (II) is reacted with compound (III) in the presence of a base to yield compound (I). The reaction of compounds (II) and (III) is carried out in an appropriate solvent. Said solvent is exemplified by aromatic hydrocarbons such as benzene, toluene and xylene, ethers such as dioxane, tetrahydrofuran and dimethoxyethane, alcohols such as methanol, ethanol and propanol, ethyl acetate, acetonitrile, pyridine, N,N-dimethylformamide, dimethylsulfoxide, chloroform, dichloromethane, 1,2-dichloroethane, 1,1,2,2-tetrachloroethane, acetone, 2-butanone and mixtures thereof. The reaction of compounds (II) and (III) is carried out in the presence of an appropriate base exemplified by alkali metal salts such as sodium hydroxide, potassium carbonate, sodium carbonate and sodium hydrogen carbonate, mines such as pyridine, triethylamine and N,N-dimethylaniline, sodium hydride and potassium hydride. The amount of these bases used is preferably about 1 to 5 mol per mol of compound (II). This reaction is carried out at temperatures normally between $-20°$ and $150°$ C., preferably between about $-10°$ and $100°$ C.

Quinoline or quinazoline derivative (I) thus obtained can be isolated and purified by known means of separation and purification such as ordinary concentration, concentration under reduced pressure, solvent extraction, crystallization, recrystallization, redissolution and chromatography.

Starting material compound (II) for the present invention can, for example, be produced as follows:

Method B

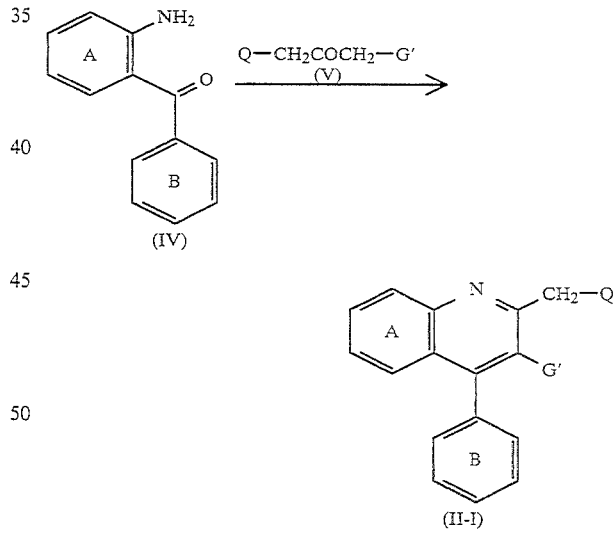

wherein G′ represents an esterified carboxyl group; the symbols have the same definitions as above. The esterified carboxyl group for G′ is exemplified by the same esterified carboxyl groups specified for G above.

In this method, 2-aminobenzophenone derivative (IV) is reacted with compound (V) in the presence of an acid to yield compound (II-1). The reaction of compounds (IV) and (V) is carried out in an appropriate solvent. This solvent is exemplified by aromatic hydrocarbons such as benzene, toluene and xylene, ethers such as dioxane, tetrahydrofuran and dimethoxyethane, N,N-dimethylformamide, dimethylsulfoxide, chloroform, dichloromethane, 1,2-dichloroethane, 1,1,2,2-tetrachloroethane and acetic acid. The reaction of compounds (IV) and (V) is carried out in the presence of an appropriate acid such as a Lewis acid such as aluminum chloride or zinc chloride, or sulfuric acid or trifluoroacetic acid. The amount of these acids used about 0.01–2.0 mol, preferably about 0.05 to 0.5 tool per mol of compound (IV). This reaction is carried out at temperatures normally between 20° and 200° C., preferably between about 30° and 150° C. Reaction time is 0.5 to 20 hours, preferably 1 to 10 hours.

Compound (II-1) thus obtained can be isolated and purified by known means of separation and purification such as ordinary concentration, concentration under reduced pressure, solvent extraction, crystallization, recrystallization, redissolution and chromatography.

Method C

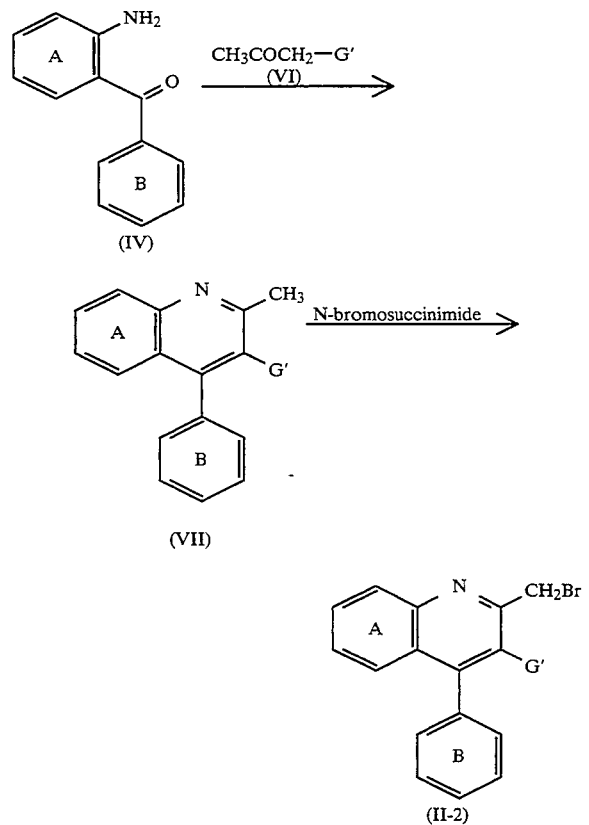

wherein the symbols have the same definitions as above.

In this method, 2-aminobenzophenone derivative (IV) is reacted with acetoacetic acid ester derivative (VI) in the presence of an acid to yield compound (VII), which is then brominated to 2-bromomethylquinoline derivative (II-2). The reaction of compounds (IV) and (VI) is carried out in the same manner as method B. Bromination of compound (VII) is carried out in an appropriate solvent by a conventional method. This solvent is exemplified by halogenated hydrocarbons such as carbon tetrachloride, chloroform, dichloromethane, 1,2-dichloroethane and 1,1,2,2-tetrachloroethane. Bromination of compound (VII) is carried out in the presence of a radical reaction initiator such as benzoyl peroxide or 2,2'-azobis(isobutyronitrile). The amount of these radical reaction initiators used is preferably about 0.001 to 0.01 equivalent mol per mol of compound (VII). This reaction is carried out at temperatures normally between 20° and 150° C., preferably between about 30° and 100° C. Reaction time is 0.5 to 20 hours, preferably 1 to 10 hours.

Compound (II-2) thus obtained can be isolated and purified by known means of separation and purification such as ordinary concentration, concentration under reduced pressure, solvent extraction, crystallization, recrystallization, redissolution and chromatography.

Method D

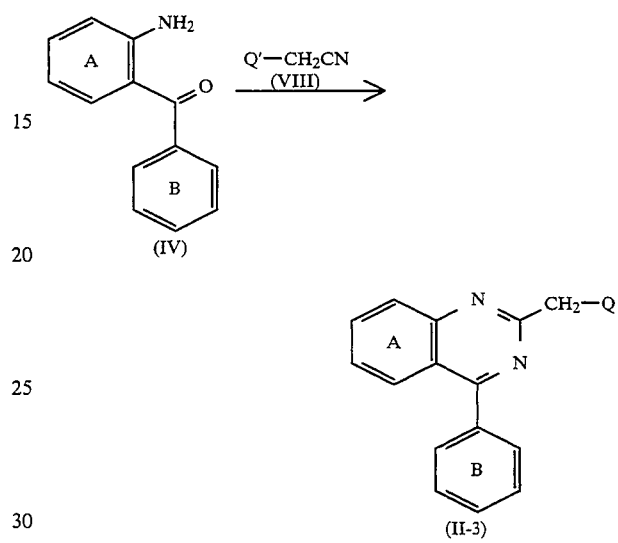

wherein Q' represents a halogen atom; the symbols have the same definitions as above. With respect to formulas (VIII) and (II-3), the halogen atom for Q' is exemplified by atoms of chlorine, bromine and iodine.

In this method, 2-aminobenzophenone derivative (IV) is reacted with halogenoacetonitrile derivative (VIII) to yield 2-halogenomethylquinazoline derivative (II-3). The reaction of compounds (IV) and (VIII) is carried out in an excess amount of compound (VIII) as a solvent in the presence of an acid. This acid is exemplified by the same acids as specified for method B above. The amount of these acids used is about 1 to 5 equivalent mol, preferably 1 to 2 mol per mol of compound (IV). Reaction time is 0.5 to 30 hours, preferably 1 to 10 hours. Reaction temperature is normally between 20° and 200° C., preferably between about 30° and 150° C.

Quinazoline derivative (II-3) thus obtained can be isolated and purified by known means of separation and purification such as ordinary concentration, concentration under reduced pressure, solvent extraction, crystallization, recrystallization, redissolution and chromatography.

Method E

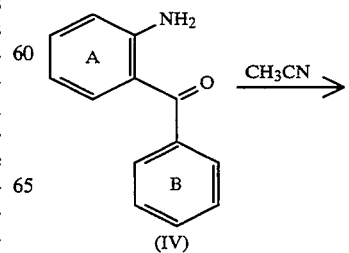

-continued

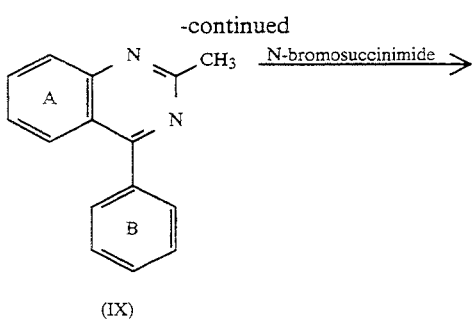

(IX)

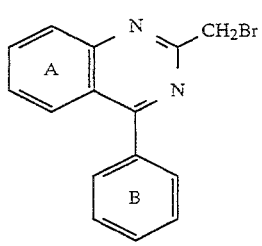

(II-4)

wherein the symbols have the same definitions as above.

In this method, 2-aminobenzophenone derivative (IV) is reacted with acetonitrile to yield 2-methylquinazoline derivative (IX), which is then brominated to 2-bromomethylquinazoline derivative (II-4). The reaction of compound (IV) and acetonitrile is carried out in the same manner as method D. Bromination of compound (IX) is carried out in the same manner as the bromination of compound (VII) by method C.

Quinazoline derivative (II-4) thus obtained can be isolated and purified by known means of separation and purification such as ordinary concentration, concentration under reduced pressure, solvent extraction, crystallization, recrystallization, redissolution and chromatography.

Method F

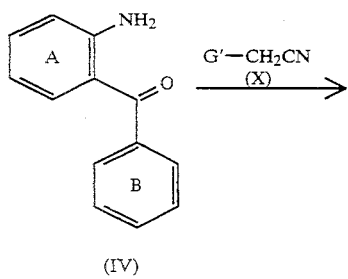

(IV)

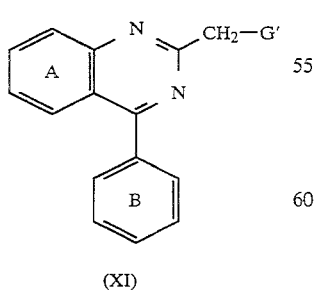

(XI)

wherein the symbols have the same definitions as above.

In this method, 2-aminobenzophenone derivative (IV) is reacted with cyanoacetic acid ester derivative (X) to yield quinazoline derivative (XI). The reaction of compounds (IV) and (X) is carried out in the same manner as method D.

Quinazoline derivative (XI) thus obtained can be isolated and purified by known means of separation and purification such as ordinary concentration, concentration under reduced pressure, solvent extraction, crystallization, recrystallization, redissolution and chromatography.

Method G

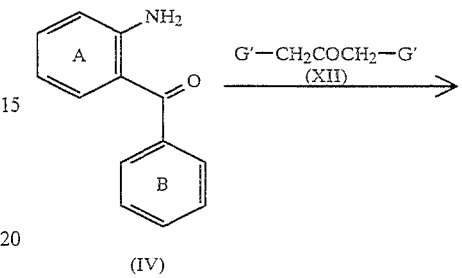

(IV)

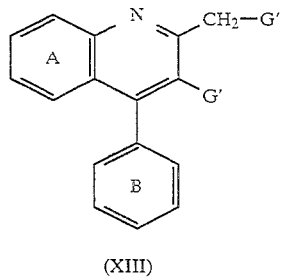

(XIII)

wherein the symbols have the same definitions as above.

In this method, 2-aminobenzophenone derivative (IV) is reacted with acetonedicarboxylic acid ester derivative (XII) to yield quinoline derivative (XIII). The reaction of compounds (IV) and (XII) is carried out in the same manner as method B.

Quinoline derivative (XIII) thus obtained can be isolated and purified by known means of separation and purification such as ordinary concentration, concentration under reduced pressure, solvent extraction, crystallization, recrystallization, redissolution and chromatography.

Method H

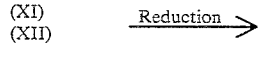

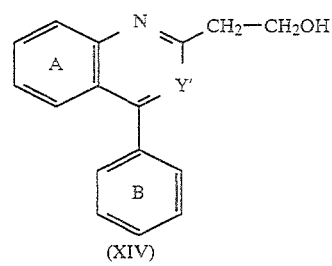

(XIV)

wherein Y' represents a nitrogen atom or C—G'; the symbols have the same definitions as above.

In this method, compounds (XI) and (XIII) as obtained by methods F and G, respectively, are subjected to a reducing reaction to yield alcohol (XIV). This reduction can be carried out by known methods such as reduction with metal hydride, reduction with metal-hydrogen complex compound, reduction with diborane or substituted diborane and catalytic hydrogenation. In other words, this reaction is carried out by treating compounds (XI) and (XIII) with a reducing agent. Reducing agents include metal-hydrogen complex compounds such as alkali metal borohydrides (e.g., sodium borohydride, lithium borohydride) and lithium aluminum hydride, metal-hydrogen compounds such as sodium hydride, organic tin compounds (e.g., triphenyltin hydride), nickel compounds, zinc compounds and other metal or metal salt compounds, catalytic reducing agents consisting of a combination of hydrogen and a transition metal catalyst such as palladium, platinum or rhodium, and diborane. This reaction is carried out in an organic solvent which does not interfere with the reaction. This solvent is exemplified by aromatic hydrocarbons such as benzene, toluene and xylene, halogenated hydrocarbons such as chloroform, carbon tetrachloride, dichloromethane, 1,2-dichloroethane and 1,1,2,2-tetrachloroethane, ethers such as diethyl ether, tetrahydrofuran and dioxane, alcohols such as methanol, ethanol, propanol, isopropanol and 2-methoxyethanol, amides such as N,N-dimethylformamide and mixtures thereof chosen as appropriate according to the kind of reducing agent. This reaction is carried out at temperatures normally between −20° and 150° C., preferably between 0° and 100° C., reaction time being about 1 to 24 hours.

Method I

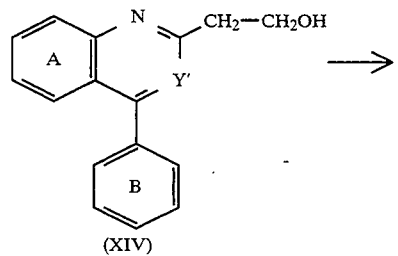

(XIV)

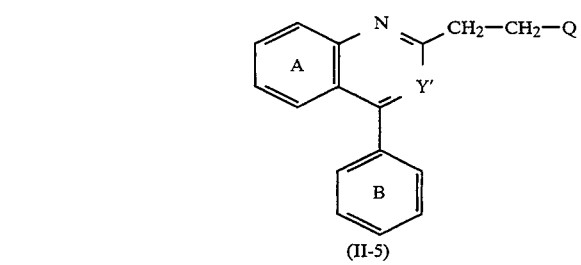

(II-5)

wherein the symbols have the same definitions as above.

In this method, compound (XIV) is reacted with a halogenating agent or a sulfonylating agent to yield compound (II-5). Preferable halogenating agents for this purpose include thionyl chloride and phosphorus tribromide. When such halogenating agents are used, compound (II-5) wherein Q is chlorine or bromine is produced. This reaction is carried out in an appropriate inert solvent (e.g., benzene, toluene, xylene, chloroform, dichloromethane) or in an excess amount of halogenating agent as a solvent at −10° to 80° C. The amount of halogenating agent used is 1 to 20 mol per tool of compound (XIV). Preferable sulfonylating agents for this purpose include mesyl chloride, tosyl chloride and benzenesulfonyl chloride. When such sulfonylating agents are used, compound (II-5) wherein Q is mesyloxy, tosyloxy or benzenesulfonyloxy, respectively, is produced. This reaction is carried out in an appropriate inert solvent (e.g., benzene, toluene, xylene, ethyl ether, ethyl acetate, tetrahydrofuran, chloroform, dichloromethane) in the presence of a base (e.g., triethylamine, N-methylmorpholine, sodium hydrogen carbonate, potassium hydrogen carbonate, sodium carbonate, potassium carbonate) at −10° to 30° C. The amount of sulfonylating agent or base used is 1 to 1.2 tool per tool of compound (XIV). It is possible to produce compound (II-5) wherein Q is iodine by reacting 1 mol of thus-obtained compound (II-5) wherein Q is chlorine, bromine or sulfonyloxy with 1 to 1.5 tool of sodium iodide or potassium iodide. In this case, the reaction can be carried out in a solvent such as acetone, methyl ethyl ketone, methanol or ethanol at 20° to 80° C.

Method J (II-1)
(II-2)
(II-3) Oxidation
(II-4)
(II-5)

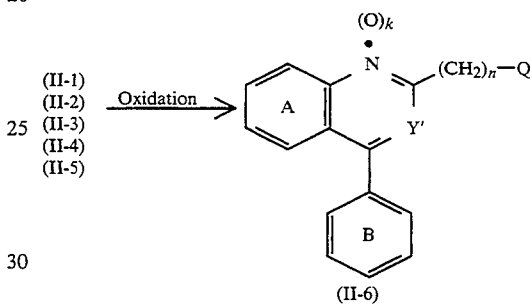

(II-6)

wherein the symbols have the same definitions as above.

In this method, compounds (II-1), (II-2), (II-3), (II-4) and (II-5) as produced by methods B, C, D, E and I, respectively, are oxidized to yield compound (II-6). This oxidation is carried out in the presence of an oxidizing agent such as m-chloroperbenzoic acid, hydrogen peroxide, perester or sodium metaperiodate in accordance with a conventional method. This oxidation is advantageously carried out in an organic solvent inert under the reaction conditions, such as a halogenated hydrocarbon (e.g., methylene chloride, chloroform, dichloroethane), a hydrocarbon (e.g., benzene, toluene) or an alcohol (e.g., methanol, ethanol, propanol). The amount of oxidizing agent used is 1 to 5 equivalent mol, preferably 1 to 3 equivalent tool per tool of compound (II-1), (II-2), (II-3), (II-4) or (II-5). Reaction temperature is between −10° and 150° C., preferably between about 0° and 100° C., reaction time being normally 0.5 to 10 hours.

Quinoline 1-oxide or quinazoline 1-oxide derivative (II-6) thus obtained can be isolated and purified by known means of separation and purification such as ordinary concentration, concentration under reduced pressure, solvent extraction, crystallization, recrystallization, redissolution and chromatography.

Compound (I) can also be produced by the following methods K, L and M.

Method K

-continued

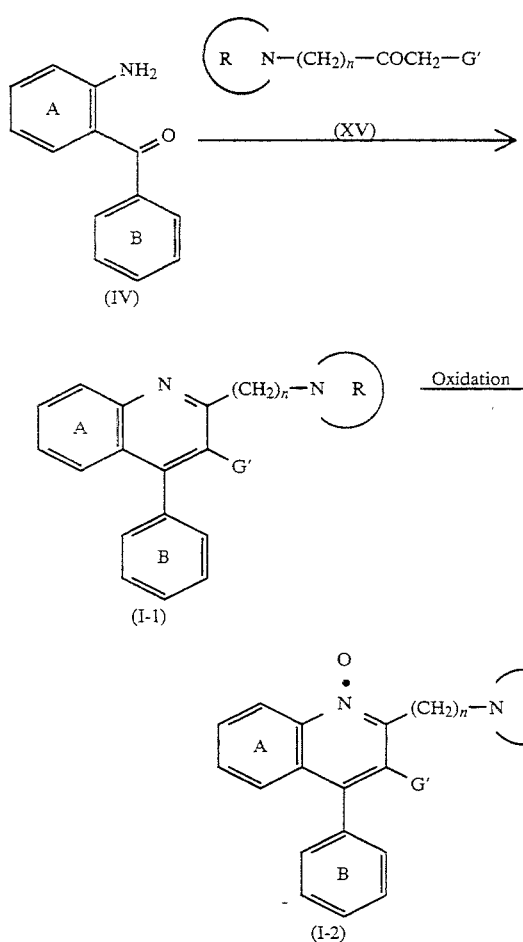

wherein the symbols have the same definitions as above.

In this method, compound (IV) is first reacted with compound (XV) to yield compound (I-1). The reaction of compounds (IV) and (XV) is carried out in the same manner as method B.

Compound (I-2) is then oxidized to compound (I-2). This oxidizing reaction is carried out in the same manner as method J.

Method L

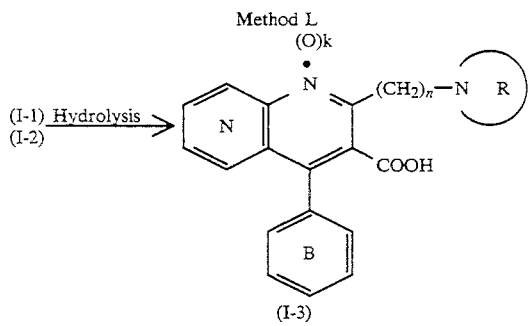

wherein the symbols have the same definitions as above.

In this method, compounds (I-1) and (I-2) are hydrolyzed to carboxylic acid derivative (I-3). This hydrolysis is carried out in water or a hydrated solvent by a conventional method. Said hydrated solvent is a mixture of water and an alcohol (e.g., methanol, ethanol), ether (e.g., tetrahydrofuran, dioxane), N,N-dimethylformamide, dimethylsulfoxide, acetonitrile or acetone.

This reaction is carried out in the presence of a base such as potassium carbonate, sodium carbonate, potassium hydroxide, sodium hydroxide or lithium or an acid such as hydrochloric acid, sulfuric acid, acetic acid or hydrobromic acid. Preferably, the acid or base is used in excess (1.2 to 6 equivalents for base, 2 to 50 equivalents for acid) per mol of compound (I-1) or (I-2). This reaction is carried out at temperatures between $-20°$ and $150°$ C., preferably between $-10°$ and $100°$ C.

Method M

In this method, compound (I) wherein rings A and B have an isopropoxy substituent is treated with titanium tetrachloride, titanium trichloride, boron trichloride, silicon tetrachloride or the like to convert the isopropoxy group to a hydroxyl group to yield compound (I-4) wherein rings A and B have a phenolic hydroxyl group as a substituent.

This reaction is carried out in an appropriate solvent. This solvent is exemplified by carbon tetrachloride, dichloromethane, chloroform, 1,2-dichloroethane, 1,1,2,2-tetrachloroethane and acetonitrile and mixtures thereof. The mount of titanium tetrachloride, boron trichloride, silicon tetrachloride etc. used is 1 to 10 equivalent mol, preferably 1 to 6 equivalent mol per isopropoxy group. This reaction is carried out at temperatures between $-50°$ and $100°$ C., preferably between $-20°$ and $80°$ C.

Compound (I) or a salt thereof as provided by the present invention, exhibiting anti-inflammatory action and antipyretic analgesic action, was shown to have excellent anti-arthritic action in an experimental model of adjuvant arthritis showing arthritic symptoms similar to those in human rheumatoid arthritis. The compound of the present invention is of low toxicity; for example, no deaths occurred in mice orally dosed with the compound synthesized in Example 2 or 16 at 100 mg/kg or in rats orally dosed with the compound synthesized in Example 16 at 200 mg/kg. With these features, the desired compounds of the present invention are applicable to all forms of arthritis showing inflammatory symptoms in the joint.

Although the dose of compound (I) of the present invention is variable according to the route of administration and symptoms of the subject patient, it can range from 5 to 1,000 mg for oral administration or from 1 to 100 mg for non-oral administration, both for adults, and this daily dose may be administered in 1 to 3 portions.

A method of testing the pharmacologic action of compound (I) of the present invention is described below. The results of such a test are also given below.

TEST EXAMPLE 1

Action Against Rat Adjuvant Arthritis

Male Lewis rats (7 weeks of age, Clea Japan) were sensitized by intracutaneous injection of 0.05 ml of Freund's complete adjuvant (0.5% dead tubercle bacillus cell suspension in liquid paraffin) at the right hind paw. The test drug (12.5 mg/kg), in suspension in 5% gum arabic, was once daily administered orally for 14 days starting just before sensitization (day 0). At days 0 and 14, the animal's left hind paw volume and body weight were measured, and percent paw swelling suppression and percent body weight gain, relative to sensitized control rats, were determined.

The results, expressed in mean ±S.E. for 6 animals in each group, were compared and statistically analyzed by Dunnett's test. Level of significance was set below 5%. As seen in Table 1, the compound of the present invention effectively suppressed paw edema and improved systemic condition as demonstrated by body weight gain.

TABLE 1

| Compound (Example No.) | Percent Swelling Suppression (%) | Body Weight Gain[1] Rate (%) |
|---|---|---|
| 1 | 65** | 5 |
| 2 | 70** | 21 |
| 3 | 55** | 16* |
| 16 | 66** | 20* |

[1] $\frac{\text{drug-treated rats} - \text{sensitized control rats}}{\text{normal rats} - \text{sensitized control rats}} \times 100(\%)$

**; $p < 0.01$, $p < 0.05$

REFERENCE EXAMPLE 1

To a mixture of 2-amino-3',4'-dimethoxy-4,5-ethylenedioxybenzophenone (6.5 g), ethyl 4-chloroacetoacetate (3.7 g) and acetic acid (60 ml), concentrated sulfuric acid (0.3 ml) was added, followed by stirring at 100° C. for 3 hours. After the reaction mixture was concentrated under reduced pressure, the residue was poured over water and alkalinized with 2N NaOH and then extracted with chloroform. The chloroform layer was washed with water and dried (MgSO$_4$), after which the solvent was distilled off under reduced pressure. The residue was subjected to silica gel column chromatography and eluted with chloroform-ethyl acetate (7:3, v/v) to yield 2-chloromethyl-4-(3,4-dimethoxyphenyl)-6,7-ethylenedioxyquinoline-3-carboxylic acid ethyl ester (5.5 g, 60%), which was then recrystallized from acetone to yield a colorless prismatic crystal having a melting point of 197° to 198° C.

Elemental analysis (for $C_{23}H_{22}NO_6Cl$): Calculated: C, 62.24; H, 5.00; N, 3.16, Found: C, 61.95; H, 5.15; N, 3.01.

REFERENCE EXAMPLES 2 THROUGH 12

The same procedure as in Reference Example 1 was followed to yield the compounds listed in Tables 2 through 3.

REFERENCE EXAMPLE 13

To a mixture of 2-amino-4,5,3',4'-tetramethoxybenzophenone, ethyl acetoacetate and acetic acid, concentrated sulfuric acid was added, followed by the same treatment as in Reference Example 1, to yield 6,7-dimethoxy-4-(3,4-dimethoxyphenyl)-2-methylquinoline-3-carboxylic acid ethyl ester (83%), which was then recrystallized from ethanol to yield a colorless prismatic crystal having a melting point of 147° to 148° C.

REFERENCE EXAMPLE 14

To a mixture of 2-amino-4,5,3',4'-tetramethoxybenzophenone, propyl acetoacetate and acetic acid, concentratd sulfuric acid was added, followed by the same treatment as in Reference Example 1, to yield 6,7-dimethoxy-4-(3,4-dimethoxyphenyl)-2-methylquinoline-3-carboxylic acid propyl ester (79%), which was then recrystallized from ethyl acetate-isopropyl ether to yield a colorless prismatic crystal having a melting point of 153° to 155° C.

REFERENCE EXAMPLE 15

To a mixture of 2-amino-4,5,3',4'-tetramethoxybenzophenone, butyl acetoacetate and acetic acid, concentrated sulfuric acid was added, followed by the same treatment as in Reference Example 1, to yield 6,7-dimethoxy-4-(3,4-dimethoxyphenyl)-2-methylquinoline-3-carboxylic acid butyl ester (53%), which was then recrystallized from ethyl acetate-hexane to yield a colorless prismatic crystal having a melting point of 119° to 120° C.

REFERENCE EXAMPLE 16

A mixture of 6,7-dimethoxy-4-(3,4-dimethoxyphenyl)-2-methylquinoline-3-carboxylic acid ethyl ester (411 rag), N-bromosuccinimide (214 mg), 2,2'-azobis(isobutyronitrile) (10 mg) and carbon tetrachloride (10 ml) was stirred under refluxing conditions for 5 hours. The reaction mixture was washed with water and dried (MgSO$_4$), after which the solvent was distilled off under reduced pressure. The residue was subjected to silica gel column chromatography and eluted with chloroform-ethyl acetate (10:1, v/v) to yield 2-bromomethyl-6,7-dimethoxy-4-(3,4-dimethoxyphenyl)quinoline-3-carboxylic acid ethyl ester (285 mg, 58%), which was then recrystallized from ethyl acetate-hexane to yield a colorless prismatic crystal having a melting point of 135° to 136° C.

Elemental analysis (for $C_{23}H_{24}NO_6Br$): Calculated: C, 56.34; H, 4.93; N, 2.86, Found: C, 55.98; H, 5.23; N, 2.62.

REFERENCE EXAMPLE 17

The same procedure as in Reference Example 16 was followed to yield 2-bromomethyl-6,7-dimethoxy-4-(3,4-dimethoxyphenyl)quinoline-3-carboxylic acid propyl ester (48%), which was then recrystallized from ethyl acetate-isopropyl ether to yield a colorless prismatic crystal having a melting point of 144° to 145° C.

Elemental analysis (for $C_{24}H_{26}NO_6Br$): Calculated: C, 57.15; H, 5.20; N, 2.78, Found: C, 56.75; H, 5.30; N, 2.68.

REFERENCE EXAMPLE 18

The same procedure as in Reference Example 16 was followed to yield 2-bromomethyl-6,7-dimethoxy-4-(3,4-dimethoxyphenyl)quinoline-3-carboxylic acid butyl ester (56%), which was then recrystallized from ethyl acetate-ether to yield a colorless prismatic crystal having a melting point of 160° to 161° C.

Elemental analysis (for $C_{25}H_{28}NO_6Br$): Calculated: C, 57.92; H, 5.44; N, 2.70, Found: C, 57.96; H, 5.53; N, 2.50.

REFERENCE EXAMPLE 19

A mixture of 2-chloromethyl-6,7-dimethoxy-4-(3,4-dimethoxyphenyl)quinoline-3-carboxylic acid ethyl ester (3.0 g), m-chloroperbenzoic acid (85%, 2.3 g) and methanol (40 ml) was stirred under refluxing conditions for 2 hours. The reaction mixture was distilled under reduced pressure to remove the solvent. The residue was poured over chloroform. The chloroform layer was washed with water and dried (MgSO$_4$), after which the solvent was distilled off under reduced pressure. The residue was subjected to silica gel column chromatography and eluted with chloroform-ethyl acetate (6:4, v/v) to yield 2-chloromethyl-6,7-dimethoxy-4-(3,4-dimethoxyphenyl)quinoline-3-carboxylic acid ethyl ester 1-oxide (2.0 g, 65%), which was then recrystallized from acetone-isopropyl ether to yield a colorless prismatic crystal having a melting point of 193° to 194° C.

Elemental analysis (for $C_{23}H_{24}NO_7Cl$): Calculated: C, 59.81; H, 5.24; N, 3.03, Found: C, 59.69; H, 5.32; N, 3.05.

REFERENCE EXAMPLE 20

To a mixture of 2-amino-4,5,3',4'-tetramethoxybenzophenone (8.0 g) and chloroacetonitrile (25 ml), powdered aluminum chloride (6.7 g) was added, followed by stirring at 100° C. for 2 hours. The reaction mixture was poured over water and extracted with chloroform. The chloroform layer was washed with water and dried ($MgSO_4$), after which the solvent was distilled off. The residue was subjected to silica gel column chromatography and eluted with chloroform-ethyl acetate (10:1, v/v) to yield 2-chloromethyl-6,7-dimethoxy-4-(3,4-dimethoxyphenyl)quinazoline (4.9 g, 52%), which was then recrystallized from acetone to yield a colorless prismatic crystal having a melting point of 183° to 184° C.

REFERENCE EXAMPLE 21

To a mixture of 2-amino-4,5,3',4'-tetramethoxybenzophenone (50.0 g), acetonedicarboxylic acid diethyl ester (35.0 g) and acetic acid (400 ml), concentrated sulfuric acid (1.5 ml) was added, followed by stirring at 100° C. for 2.5 hours. The reaction mixture was concentrated under reduced pressure, and the residue was poured over water, neutralized with a saturated aqueous sodium hydrogen carbonate solution and then extracted with chloroform. The chloroform layer was washed with water and dried ($MgSO_4$), after which the solvent was distilled off under reduced pressure. The residual crystal was recrystallized from ethanol to yield 6,7-dimethoxy-4-(3,4-dimethoxyphenyl)- 3-ethoxycarbonylquinoline-2-acetic acid ethyl ester (55.6 g, 73%) as a colorless prismatic crystal having a melting point of 146° to 147° C.

REFERENCE EXAMPLE 22

To a mixture of 2-amino-4,5,3',4'-tetramethoxybenzophenone (6.3 g) and cyanoacetic acid methyl ester (23 ml), powdered aluminum chloride (5.3 g) was added, followed by stirring at 100° C. for 2.5 hours. The reaction mixture was poured over water and extracted with ethyl acetate. The ethyl acetate layer was washed with water and dried ($MgSO_4$), after which the solvent was distilled off. The residue was subjected to silica gel column chromatography and eluted with hexane-ethyl acetate (4:1, v/v) to yield 6,7-dimethoxy-4-(3,4-dimethoxyphenyl)quinazoline-2-acetic acid methyl ester (4.4 g, 55%), which was then recrystallized from isopropyl ether to yield a colorless needle crystal having a melting point of 152° to 153° C.

REFERENCE EXAMPLE 23

A mixture of sodium iodide (1.68 g) and 2-butanone (15 ml) was stirred at 80° C. for 1 hour, after which 2-chloromethyl-6,7-dimethoxy-4-(3,4-dimethoxyphenyl)quinoline-3-carboxylic acid ethyl ester (2.68 g) was added, followed by stirring at 80° C. for 12 hours. The reaction mixture was concentrated under reduced pressure, and the residue was poured over water and then extracted with ethyl acetate. The ethyl acetate layer was washed with water and dried ($MgSO_4$), after which the solvent was distilled off under reduced pressure. The residue was subjected to silica gel column chromatography and eluted with chloroform-ethyl acetate (1:1, v/v) to yield—6,7-dimethoxy-4-(3,4-dimethoxyphenyl)-2-iodomethylquinoline-3-carboxylic acid ethyl ester (1.4 g, 58%), which was then recrystallized from ethyl acetate-hexane to yield a colorless prismatic crystal having a melting point of 170° to 171° C.

REFERENCE EXAMPLE 24

A solution of 6,7-dimethoxy-4-(3,4-dimethoxyphenyl)-3-ethoxycarbonylquinoline-2-acetic acid ethyl ester (5.8 g) in tetrahydrofuran (100 ml) was added drop by drop at 0° C. to a suspension of lithium aluminum hydride (0.455 g) in tetrahydrofuran (50 ml). After the reaction mixture was stirred at 0° C. for 1 hour, water (2.5 ml) was added drop by drop, followed by stirring for 30 more minutes. After the insoluble solid was filtered off, the filtrate was concentrated under reduced pressure. The residue was subjected to silica gel column chromatography and eluted with chloroform-ethyl acetate (1:1, v/v) to yield 6,7-dimethoxy-4-(3,4-dimethoxyphenyl)-2-(2-hydroxyethyl)quinoline-3-carboxylic acid ethyl ester (1.75 g, 33%), which was then recrystallized from ethyl acetate-hexane to yield a colorless prismatic crystal having a melting point of 150° to 151° C.

REFERENCE EXAMPLE 25

Phosphorus tribromide ($PBr_3$) (1.0 g) was added drop by drop to a solution of 6,7-dimethoxy-4-(3,4-dimethoxyphenyl)-2-(2-hydroxyethyl)quinoline-3-carboxylic acid ethyl ester (1.7 g) in benzene (50 ml) at room temperature. After stirring at 80° C. for 1 hour, the reaction mixture was poured over ice water, neutralized with a saturated aqueous solution of sodium hydrogen carbonate and then extracted with chloroform. The chloroform layer was washed with water and then dried ($MgSO_4$), after which the solvent was distilled off. The residue was subjected to silica gel column chromatography and eluted with chloroform-ethyl acetate (1:1, v/v) to yield 2-(2-bromoethyl)-6,7-dimethoxy-4-(3,4-dimethoxyphenyl)quinoline-3-carboxylic acid ethyl ester (0.49 g, 26%), which was then recrystallized from ethyl acetate-hexane to yield a colorless prismatic crystal having a melting point of 132° to 133° C.

REFERENCE EXAMPLES 26 THROUGH 32

The same procedure as in Reference Example 1 was followed to yield the compounds listed in Table 4.

REFERENCE EXAMPLE 33

A mixture of 4-bromobutyric acid benzyl ester (23.7 g), imidazole (8.1 g), potassium carbonate (14.0 g) and acetone (400 ml) was stirred under refluxing conditions for 6 hours. After the reaction mixture was cooled to room temperature, the insoluble solid was filtered off, the filtrate was concentrated. The residual oily substance was subjected to silica gel column chromatography and eluted with ethyl acetate-methanol (20:1, v/v) to yield 4-(1-imidazolyl)butyric acid benzyl ester (7.3 g, 33%) as an oily substance.

NMR (δ ppm in $CDCl_3$): 2.11 (2H, m), 2.34 (2H, t, J=6.8 Hz), 3.99 (2H, t, J=6.8 Hz), 5.12 (2H, s), 6.87 (1H, S), 7.05 (1H, s), 7.30–7.40 (5H, m).

REFERENCE EXAMPLE 34

The same procedure as in Reference Example 33 was followed to yield 4-(1,2,4-triazol-1-yl)butyric acid benzyl ester (yield 88%) as an oily substance.

NMR (δ ppm in $CDCl_3$): 2.14–2.42 (4H, m), 4.24 (2H, t, J=6.4 Hz), 5.13 (2H, s), 7.30–7.43 (5H, m), 7.94 (1H, s), 7.99 (1H, s).

REFERENCE EXAMPLE 35

The same procedure as in Reference Example 33 was followed to yield 5-(1-imidazolyl)valeric acid benzyl ester as an oily substance by reaction of 5-bromovaleric acid benzyl ester and imidazole.

NMR (δ ppm in CDCl$_3$): 1.55–1.90 (4H, m), 2.38 (2H, t, J=6.8 Hz), 3.93 (2H, t, J=7.0 Hz), 5.11 (2H, s), 6.87 (1H, s), 7.05 (1H, s), 7.25–7.50 (5H, m), 7.94 (1H, s), 7.99 (1H, s).

REFERENCE EXAMPLE 36

A mixture of 4-(1-imidazolyl)butyric acid benzyl ester (7.4 g), 5% palladium-carbon (1.0 g) and ethanol (400 ml) was catalytically reduced at room temperature under 1 atm. After the catalyst was filtered off, the filtrate was concentrated under reduced pressure, and the residual crystal was recrystallized from ethanol, to yield 4-(1-imidazolyl)butyric acid (3.4 g, 75%) as a colorless prismatic crystal having a melting point of 125° to 126° C.

REFERENCE EXAMPLE 37

4-(1,2,4-Triazol-1-yl)butyric acid benzyl ester was catalytically reduced in the same manner as in Reference Example 36 to yield 4-(1,2,4-triazol-1-yl)butyric acid, which was then recrystallized from ethanol to yield a colorless prismatic crystal having a melting point of 137° to 138° C.

REFERENCE EXAMPLE 38

5-(1-Imidazolyl)valeric acid benzyl ester was catalytically reduced in the same manner as in Reference Example 36 to yield 5-(1-imidazolyl)valeric acid, which was then recrystallized from ethanol to yield a colorless prismatic crystal having a melting point of 157° to 158° C.

REFERENCE EXAMPLE 39

To a suspension of 4-(1-imidazolyl)butyric acid (0.5 g) in tetrahydrofuran (35 ml), 1,1'-carbonyldiimidazole (0.578 g) was added, followed by stirring at room temperature for 6 hours. After magnesium salt of malonic acid monoethyl ester [Mg(OCOCH$_2$COOC$_2$H$_5$)$_2$] (1.02 g) was added, the mixture was stirred at room temperature for 18 more hours. After the reaction mixture was concentrated under reduced pressure, the residue was dissolved in dichloromethane. The dichloromethane layer was washed with water and dried (MgSO$_4$), after which the solvent was distilled off. The residual oily substance was subjected to silica gel column chromatography and eluted with chloroform-methanol (30:1, v/v) to yield 6-(1-imidazolyl)-3-oxohexanoic acid ethyl ester (0.32 g, 44%) as an oily substance.

NMR (δ ppm in CDCl$_3$): 1.28 (3H, t, J=7.4 Hz), 2.08 (2H, m), 2.53 (2H, t, J=6.6 Hz), 3.41 (2H, s), 4.00 (2H, t, J=6.6 Hz), 4.19 (2H, q, J=7.4 Hz), 6.91 (1H, s), 7.07 (1H, s), 7.46 (1H, s).

REFERENCE EXAMPLE 40

The same procedure as in Reference Example 39 was followed to yield 6-(1,2,4-triazol-1-yl)-3-oxohexanoic acid ethyl ester, as an oily substance, from 4-(1,2,4-triazol-1-yl)butyric acid.

NMR (δ ppm in CDCl$_3$): 1.28 (3H, t, J=7.2 Hz), 2.19 (2H, m), 2.59 (2H, t, J=6.6 Hz), 3.43 (2H, s), 4.19 (2H, q, J=7.2 Hz), 4.23 (2H, t, J=6.6 Hz), 7.94 (1H, s), 8.07 (1H, s).

REFERENCE EXAMPLE 41

The same procedure as in Reference Example 39 was followed to yield 7-(1-imidazolyl)-3-oxoheptanoic acid ethyl ester, as an oily substance, from 5-(1-imidazolyl)-valeric acid.

NMR (δ ppm in CDCl$_3$): 1.27 (3H, t, J=7.4 Hz), 1.50–1.90 (4H, m), 2.58 (2H, t, J=6.6 Hz), 3.41 (2H, s), 3.95 (2H, t, J=7.0 Hz), 4.19 (2H, q, J=7.4 Hz), 6.90 (1H, s), 7.06 (1H, s), 7.47 (1H, s).

REFERENCE EXAMPLE 42

The same procedure as in Reference Example 1 was followed to yield 2-chloromethyl-6,7-dimethoxy-4-(4-methoxy-3-propoxyphenyl)quinoline-3-carboxylic acid ethyl ester which was then recrystallized from ethanol to yield a colorless prismatic crystal having a melting point of 126° to 128° C.

REFERENCE EXAMPLE 43

To a mixture of methyl 6,7-dimethoxy-4-(3,4-dimethoxyphenyl)quinazoline-2-acetic acid methyl ester (4.0 g), sodium borohydride (1.9 g) and tetrahydrofuran (80 ml), methanol (15 ml) was added dropwise under continuous reflux, followed by refluxing for 2 hours. The reaction mixture was poured into water and extracted with ethyl acetate. The ethyl acetate layer was washed with water, dried (MgSO$_4$) and concentrated under reduced pressure to yield 6,7-dimethoxy-4-(3,4-dimethoxyphenyl)-2-(2-hydroxyethyl) quinazoline (3.0 g, 81%). Recrystallization from ethyl acetate gave a colorless needle crystal having a melting point of 165° to 166° C.

REFERENCE EXAMPLE 44

The same procedure as in Reference Example 25 was followed to yield 2-(2-bromoethyl)-6,7-dimethoxy-4-(3,4-dimethoxyphenyl) quinazoline, which was then recrystallized from ethyl acetate to yield a colorless needle crystal having a melting point of 166° to 167° C.

EXAMPLE 1

Oily sodium hydride (60%, 0.323 g) was added to a solution of 2-ethylimidazole (0.776 g) in N,N-dimethylformamide (30 ml), followed by stirring at room temperature for 15 minutes. Then 2-chloromethyl-6,7-dimethoxy-4-(3,4-dimethoxyphenyl)quinoline-3-carboxylic acid ethyl ester (3.0 g) was added. After stirring at 80° C. for 1 hour, the reaction mixture was poured over water, and the separating crystal was collected by filtration, which was then recrystallized from ethanol to yield 6,7-dimethoxy-4-(3,4-dimethoxyphenyl)-2-(2-ethylimidazol-1-ylmethyl)quinoline-3-carboxylic acid ethyl ester (2.5 g, 74%) as a colorless prismatic crystal having a melting point of 163° to 164° C.

EXAMPLES 2 THROUGH 11

The same procedure as in Example 1 was followed to yield the compounds listed in Tables 5 and 6.

EXAMPLE 12

Oily sodium hydride (60%, 0.044 g) was added to a solution of imidazole (0.075 g) in N,N-dimethylformamide (5 ml), followed by stirring at room temperature for 15 minutes. Then 2-(2-bromoethyl)-6,7-dimethoxy-4-(3,4-dimethoxyphenyl)quinoline-3-carboxylic acid ethyl ester (0.4 g) was added. After stirring at 80° C. for 1 hour, the reaction mixture was poured over water and extracted with ethyl acetate. The ethyl acetate layer was washed with water and then dried (MgSO$_4$), after which the solvent was distilled off. The residue was subjected to silica gel column chromatography and eluted with ethyl acetate-methanol (10:1, v/v) to yield 2-[2-(1-imidazolyl)ethyl]-6,7-dimethoxy-4-(3,4-dimethoxyphenyl)quinoline-3-carboxylic acid ethyl ester (0.295 g, 66%), which was then recrystallized from ethyl acetate-hexane to yield a colorless prismatic crystal having a melting point of 173° to 174° C.

EXAMPLES 13 THROUGH 15

The same procedure as in Example 12 was followed to yield the compounds listed in Table 6.

EXAMPLE 16

Oily sodium hydride (60%, 0.323 g) was added to a solution of 1H-1,2,4-triazole (0.558 g) in N,N-dimethylformamide (30 ml), followed by stirring at room temperature for 15 minutes. Then 2-chloromethyl-6,7-dimethoxy-4-(3,4-dimethoxyphenyl)quinoline-3-carboxylic acid ethyl ester (3.0 g) was added. After stirring at 80° C. for 1 hour, the reaction mixture was poured over water and extracted with ethyl acetate. The ethyl acetate layer was washed with water and then dried (MgSO$_4$), after which the solvent was distilled off. The residue was subjected to silica gel column chromatography and eluted with chloroform-methanol (40:1, v/v) to yield 6,7-dimethoxy-4-(3,4-dimethoxyphenyl)-2-(1,2,4-triazol- 1-ylmethyl)quinoline-3-carboxylic acid ethyl ester (1.7 g, 53%), which was then recrystallized from ethyl acetate-hexane to yield a colorless prismatic crystal having a melting point of 176 to 177° C.

EXAMPLE 17

From the second fraction in the column chromatography in Example 16 was obtained 6,7-dimethoxy-4-(3,4-dimethoxyphenyl)-2-(1,2,4-triazol-4 -ylmethyl)-quinoline-3-carboxylic acid ethyl ester (0.07 g, 2%), which was then recrystallized from ethyl acetate-hexane to yield a colorless prismatic crystal having a melting point of 226° to 227° C.

EXAMPLE 18

The same procedure as in Example 16 was followed to yield 6,7-dimethoxy-4-(4-methoxyphenyl)-2-(1,2,4-triazol-1-ylmethyl)quinoline-3-carboxylic acid ethyl ester, which was then recrystallized from ethyl acetate-hexane to yield a colorless prismatic crystal having a melting point of 150° to 151° C.

EXAMPLE 19

From the second fraction in the column chromatography in Example 18 was obtained 6,7-dimethoxy-4-(4-methoxyphenyl)-2-(1,2,4-triazol-4-ylmethyl)quinoline-3-carboxylic acid ethyl ester, which was then recrystallized from ethyl acetate-hexane to yield a colorless needle crystal having a melting point of 218° to 219° C.

EXAMPLES 20 THROUGH 28

The same procedure as in Example 12 was followed to yield the compounds listed in Table 7.

EXAMPLE 29

To a solution of 6,7-dimethoxy-4-(4-isopropoxy-3-methoxyphenyl)-2-(1,2,4-triazol-1-ylmethyl)quinoline-3-carboxylic acid ethyl ester (55.6 mg) in dichloromethane (2 ml), titanium tetrachloride (TIC14) (125 mg) was added at 0° C., followed by stirring at the same temperature for 6 hours. The reaction mixture was poured over water and extracted with chloroform. The chloroform layer was washed by sequential additions of a saturated aqueous sodium hydrogen carbonate solution and water and then dried (MgSO$_4$), after which the solvent was distilled off. The residual oily substance was subjected to silica gel column chromatography and eluted with ethyl acetate-chloroform (3:2, v/v) to yield 6,7-dimethoxy-4-(4-hydroxy-3-methoxyphenyl)-2-(1,2,4-triazol-1-ylmethyl)quinoline-3-carboxylic acid ethyl ester (24.5 mg, 48%) which was then recrystallized from ethyl acetate-hexane having a melting point of 176° to 178° C.

NMR (δ ppm in CDCl$_3$): 0.88 (3H, t, J=7.2 Hz), 3.80 (3H, s), 3.88 (3H, s), 3.96 (2H, q, J=7.2 Hz), 4.05 (3H, s), 5.73 (2H, s), 5.80 (1H, broad s), 6.80–7.06 (4H, m), 7.42 (1H, s), 7.94 (1H, s), 8.27 (1H, s).

EXAMPLES 30 THROUGH 32

The same procedure as in Example 29 was followed to yield the compounds listed in Table 8.

EXAMPLE 33

To a solution of 4-(3,4-diisopropoxyphenyl)-6,7-dimethoxy-2-(1,2,4-triazol-1-ylmethyl)quinoline-3-carboxylic acid ethyl ester (116.0 rag) in dichloromethane (2.5 ml), titanium tetrachloride (TICl$_4$) (288 mg) was added at 0° C., followed by stirring at the same temperature for 6 hours. The reaction mixture was poured over water and extracted with chloroform. The chloroform layer was washed by sequential additions of a saturated aqueous sodium hydrogen carbonate solution and water and then dried (MgSO$_4$), after which the solvent was distilled off. The residual oily substance was subjected to silica gel column chromatography and eluted with chloroform-ethyl acetate (7:3, v/v) to yield 4-(3,4-dihydroxyphenyl)-6,7-dimethoxy-2-(1,2,4-triazol-1-ylmethyl)quinoline-3-carboxylic acid ethyl ester (20.0 mg, 21%) having a melting point of 122° to 124° C.

NMR (δ ppm in CDCl$_3$): 0.78 (3H, t, J=7.0 Hz), 3.78 (3H, s), 3.86 (2H, q, J=7.0 Hz), 4.00 (3H, s), 5.71 (2H, s), 6.60 (1H, broad s), 6.68–6.79 (2H, m), 6.92 (1H, s), 6.97 (1H, d, J=8.0 Hz), 7.37 (1H, s), 7.95 (1H, s), 8.35 (1H, s), 8.70 (1H, broad s).

EXAMPLE 34

To a solution of 4-(3,4-diisopropoxyphenyl)-6-isopropoxy-7-methoxy-2-(1,2,4-triazol-1-ylmethyl)quinoline-3-carboxylic acid ethyl ester (96.0 rag) in dichloromethane (1.0 ml), titanium tetrachloride (TICl$_4$) (316 mg) was added at 0° C., followed by stirring at the same temperature for 10 hours. The reaction mixture was poured over water and extracted with ethyl acetate. The ethyl acetate layer was washed by sequential additions of a saturated aqueous sodium hydrogen carbonate solution and water and then dried (MgSO$_4$), after which the solvent was distilled off. The residual oily substance was subjected to silica gel column chromatography and eluted with ethyl acetate-methanol (10:1, v/v) to yield 4-(3,4-dihydroxyphenyl)-6-hydroxy-7-methoxy-2-(1,2,4-triazol-1-ylmethyl)quinoline-3-carboxylic acid ethyl ester (19.0 mg, 26%) having a melting point of 264° to 266° C.

NMR (δ ppm in CDCl$_3$): 0.88 (3H, t, J=7.0 Hz), 3.93 (2H, q, J=7.0 Hz), 3.94 (3H, s), 5.63 (2H, s), 6.52 (1H, dd, J=8.2 & 2.2 Hz), 6.67 (1H, d, J=2.2 Hz), 6.85 (1H, d, J=8.2 Hz), 6.98 (1H, s), 7.29 (1H, s), 7.94 (1H, s), 8.57 (1H, s), 9.17 (1H, s), 9.21 (1H, s), 10.00 (1H, s).

EXAMPLE 35

To a mixture of 2-amino-4,5,3',4'-tetramethoxybenzophenone (453 mg), 6-(1-imidazolyl)-3-oxohexanoic acid ethyl ester (320 mg) and acetic acid (5 ml), concentrated sulfuric acid (0.03 ml) was added, followed by stirring at 100° C. for 2 hours. After the reaction mixture was concentrated under reduced pressure, the residue was poured over water, alkalinized with 2N sodium hydroxide and then extracted with chloroform. The chloroform layer was washed with water and dried (MgSO$_4$), after which the solvent was distilled off. The residual oily substance was subjected to silica gel column chromatography and eluted with chloroform-methanol (50:1, v/v) to yield 6,7-dimethoxy-4-(3,4-dimethoxyphenyl)-2-[3-(1-imidazolyl)propyl]quinoline-3-carboxylic acid ethyl ester (310.0 mg, 43%), which was then recrystallized from ethyl acetate-hexane to yield a colorless prismatic crystal having a melting point of 164° to 165° C.

EXAMPLE 36

The same procedure as in Example 35 was followed to yield 6,7-dimethoxy-4-(3,4-dimethoxyphenyl)-2-[3-(1,2,4-triazol- 1-yl)propyl]quinoline-3-carboxylic acid ethyl ester, which was then recrystallized from ethanol to yield a colorless prismatic crystal having a melting point of 141° to 142° C.

EXAMPLE 37

The same procedure as in Example 35 was followed to yield 6,7-dimethoxy-4-(3,4-dimethoxyphenyl)-2-[4-(1-imidazolyl)butyl]quinoline-3-carboxylic acid ethyl ester, which was then recrystallized from ethyl acetate-hexane to yield a colorless prismatic crystal having a melting point of 119° to 120° C.

EXAMPLE 38

A mixture of 6,7-dimethoxy-4-(3,4-dimethoxyphenyl)-2-(1,2,4-triazol-1-ylmethyl)quinoline-3-carboxylic acid ethyl ester (3.0 g), 2N sodium hydroxide (15.6 ml) and ethanol (50 ml) was stirred under refluxing conditions for 8 hours. The reaction mixture was cooled with ice and adjusted to pH 5 with 2N hydrochloric acid, after which it was concentrated under reduced pressure. The residue was dissolved in ethanol, and the insoluble substances were filtered off. After the filtrate was concentrated, the residual oily substance was subjected to silica gel column chromatography and eluted with chloroform-methanol (4:1, v/v) to yield 6,7-dimethoxy-4-(3,4-dimethoxyphenyl)-2-(1,2,4-triazol- 1-ylmethyl)quinoline-3-carboxylic acid (1.3 g, 46%), which was then recrystallized from dichloromethane-ethanol to yield a colorless prismatic crystal having a melting point of 270° to 271° C. (decomposed).

EXAMPLE 39

Oily sodium hydride (60%, 0.156 g) was added to a solution of 1H-1,2,4-triazole (0.27 g) in N,N-dimethylformamide (DMF) (20 ml), followed by stirring at room temperature for 15 minutes. Then 2-chloromethyl-6,7-dimethoxy-4-(3,4-dimethoxyphenyl)quinoline-3-carboxylic acid ethyl ester 1-oxide (1.5 g) was added, followed by stirring at 80° C. for 45 minutes. The reaction mixture was poured over water and extracted with dichloromethane. The dichloromethane layer was washed with water and then dried (MgSO$_4$), after which the solvent was distilled off. The residual oily substance was subjected to silica gel column chromatography .and eluted with chloroform-methanol (30:1, v/v) to yield 6,7-dimethoxy-4-(3,4-dimethoxyphenyl)-2-(1,2,4-triazol-1-ylmethyl)quinoline-3-carboxylic acid ethyl ester 1-oxide (0.8 g, 50%), which was then recrystallized from dichloromethane-hexane to yield a colorless prismatic crystal having a melting point of 221° to 222° C.

EXAMPLE 40

The same procedure as in Example 16 was followed to yield 6,7-dimethoxy-4-(3-propoxy-4-methoxyphenyl)-2-(1,2,4-triazol-1-ylmethyl)quinoline-3-carboxylic acid ethyl ester, which was then recrystallized from ethanol to yield a colorless prismatic crystal having a melting point of 127° to 128° C.

EXAMPLE 41

From the second fraction in the column chromatography in Example 40 was obtained 6,7-di-methoxy-4-(3-propoxy-4-methoxyphenyl)-2-(1,2,4-triazol-4-ylmethyl)quinoline-3-carboxylic acid ethyl ester which was then recrystallized from ethanol to yield a colorless needle crystal having a melting point of 154° to 155° C.

EXAMPLE 42

The same procedure as in Example 16 was followed to yield 4-(3,4-dimethoxyphenyl)-6,7-ethylenedioxy-2-(1,2,4-triazol- 1-ylmethyl)quinoline-3-carboxylic acid ethyl ester, which was then recrystallized from ethanol to yield a colorless needle crystal having a melting point of 138° to 140° C.

EXAMPLE 43

From the second fraction in the column chromatography in Example 42 was obtained 4-(3,4-dimethoxyphenyl)-6,7-ethylenedioxy-2-(1,2,4-triazol-4-ylmethyl)-quinoline-3-carboxylic acid ethyl ester which was then recrystallized from ethanol to yield a colorless needle crystal having a melting point of 237° to 239° C.

EXAMPLE 44

The same procedure as in Example 16 was followed to yield 6,7-dimethoxy-4-(3,4-dimethoxyphenyl)-2-(1,2,3-triazol-1-ylmethyl)quinoline-3-carboxylic acid ethyl ester, which was then recrystallized from ethanol-dichloroethane to yield a colorless prismatic crystal having a melting point of 195° to 196° C.

Elemental analysis (for $C_{25}H_{26}N_4O_6 \cdot \frac{1}{4}C_2H_5OH$), Calculated: C, 62.50; H, 5.66; N, 11.43, Found: C, 62.29; H, 5.53; N, 11.30.

EXAMPLE 45

From the second fraction in the column chromatography in Example 44 was obtained 6,7-dimethoxy-4-(3,4-dimethoxyphenyl)-2-(1,2,3-triazol-2-ylmethyl)-quinoline-3-carboxylic acid ethyl ester, which was then recrystallized from ethanol-dichloroethane to yield a colorless prismatic crystal having a melting point of 163° to 164° C.

Elemental analysis (for $C_{25}H_{26}N_4O_6 \cdot \frac{1}{2}C_2H_5OH$), Calculated: C, 62.27; H, 5.83; N, 11.17, Found: C, 61.98; H, 5.69; N, 11.10.

EXAMPLE 46

From the second fraction in the column chromatography in Example 25 was obtained 6,7-dimethoxy-4-(3-isopropoxy-4-methoxyphenyl)-2-(1,2,4-triazol-4-ylmethyl)quinoline-3-carboxylic acid ethyl ester, which was then recrystallized from ethyl acetate-hexane to yield a colorless prismatic crystal having a melting point of 170° to 171° C.

EXAMPLE 47

From the second fraction in the column chromatography in Example 26 was obtained 6,7-dimethoxy-4-(4-isopropoxy-3-methoxyphenyl)-2-(1,2,4-triazol-4-ylmethyl)quinoline-3-carboxylic acid ethyl ester, which was then recrystallized from ethyl acetate-hexane to yield a colorless prismatic crystal having a melting point of 178° to 179° C.

EXAMPLE 48

Oily sodium hydride (60% 0.323 g) was added to a solution of 2-hydroxypyridin (0.277 g) in N,N-dimethylformamide (10 ml), followed by stirring at room temperature for 15 minutes. Then 2-iodomethyl-6,7-dimethoxy-4-(3,4-dimethoxyphenyl)quinoline-3-carboxylic ethyl ester (1.2 g) was added. After stirring at room temperature for 8 hours. The reaction mixture was poured over water and extracted with ethyl acetate. The ethyl acetate layer was washed with water and then dried (MgSO₄), after which the solvent was distilled off.

The residue subjected to silica gel chromatography and eluted with ethyl acetate-chloroform (10:1, v/v) to yield 2-(1,2-dihydro-2-oxopyridin-1-ylmethyl)-6,7-dimethoxy-4-(3,4-dimethoxyphenyl)quinoline-3-carboxylic acid ethyl ester (0.64 g, 57%), which was then recrystallized from ethanol to a yield a colorless prismatic crystal having a melting point of 154° to 156° C.

EXAMPLE 49

The same procedure as in Example 12 was followed to yield 2-[2-(1-imidazolyl)ethyl]-6,7-dimethoxy-4-(3,4-dimethoxyphenyl)quinazoline, which was then recrystallized from ethyl acetate to yield a colorless prismatic crystal having a melting point of 147° to 148° C.

EXAMPLE 50

The same procedure as in Example 1 was followed to yield 2-(benzimidazol-1-ylmethyl)-6,7-dimethoxy-4-(3,4-dimethoxyphenyl)quinoline-3-carboxylic acid ethyl ester by reaction of 2-bromomethyl-6,7-dimethoxy-4-(3,4-dimethoxyphenyl)quinoline-3-carboxylic acid ethyl ester with benzimidazole, which was then recrystallized from ethanol to yield a colorless prismatic crystal having a melting point of 99° to 100° C.

EXAMPLE 51

The same procedure as in Example 16 was followed to yield 6,7-dimethoxy-4-(3,4-dimethoxyphenyl)-2-(1,2,4-triazol- 1-ylmethyl)quinoline-3-carboxylic acid methyl ester by reaction of 2-chloromethyl-6,7-dimethoxy-4-(3,4-dimethoxyphenyl)quinoline-3-carboxylic acid methyl ester with 1H-1,2,4-triazole, which was then recrystallized from ethanol to yield a colorless prismatic crystal having a melting point of 218° to 220° C.

EXAMPLE 52

The same procedure as in Example 1 was followed to yield 6,7-dimethoxy-4-(3,4-dimethoxyphenyl)-2-(imidazol-1-ylmethyl)quinoline-3-carboxylic acid propyl ester by reaction of 2-bromomethyl-6,7-dimethoxy-4-(3,4-dimethoxyphenyl)quinoline-3-carboxylic acid propyl ester with imidazole, which was then recrystallized from ethanol to yield a colorless prismatic crystal having a melting point of 166° to 168° C.

EXAMPLE 53

The same procedure as in Example 1 was followed to yield 6,7-dimethoxy-4-(3,4-dimethoxyphenyl)-2-(imidazol- 1-ylmethyl)quinoline-3-carboxylic acid butyl ester by reaction of 2-bromomethyl-6,7-dimethoxy-4-(3,4-dimethoxyphenyl)quinoline-3-carboxylic acid butyl ester with imidazole, which was then recrystallized from ethanol to yield a colorless prismatic crystal having a melting point of 140° to 141° C.

EXAMPLE 54

The same procedure as in Example 16 was followed to yield 6-chloro-4-phenyl-2-(1,2,4-triazol-1-ylmethyl)-quinoline-3-carboxylic acid ethyl ester by reaction of 6-chloro-2-chloromethyl-4-phenylquinoline-3-carboxylic acid ethyl ester by reaction of 6-chloro-2-chloromethyl-4-phenylquinoline-3-carboxylic acid ethyl ester with 1H-1,2,4-triazole, which was then recrystallized from ethanol to yield a colorless prismatic crystal having a melting point of 114° to 116° C.

EXAMPLE 55 THROUGH 62

The same procedure as in Example 1 was followed to yield the compounds listed in Table 9.

EXAMPLE 63

A solution of HCl in ethanol (23%, 0.172g) was added dropwise to a suspension of 6,7-dimethoxy-4-(3-isopropoxy-4-methoxyphenyl)-2-(1,2,4-triazol-1-ylmethyl) quinoline-3-carboxylic acid ethyl ester (0.5 g) in ethanol (10ml)-dichloromethane (2 ml) at room temperature. The mixture was stirred at the same temperature for 15 minutes and concentrated under reduced pressure. The residue was treated with isopropyl ether to yield solid, which was recrystallized from ethanol to yield 6,7-dimethoxy-4-(3-isopropoxy-4-methoxyphenyl)-2-(1,2,4-triazol-1-ylmethyl) quinoline-3-carboxylic acid ethyl ester hydrochloride (0.211g, 39%) as yellow crystals having melting point of 93 to 95° C.

TABLE 2

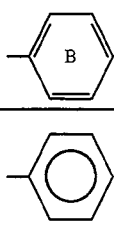

| Reference Example No. | $R^1$, $R^2$ | B | G | Yield (%) | Melting Point (°C.) | Recrystallization Solvent |
|---|---|---|---|---|---|---|
| 2 | 6-Cl, H | phenyl | COOC$_2$H$_5$ | 61 | 105–106 | Ethanol-water |
| 3 | 6-Cl, H | 4-Cl-phenyl | COOC$_2$H$_5$ | 42 | 140–141 | Ethyl acetate-hexane |
| 4 | 6-CH$_3$, H | phenyl | COOC$_2$H$_5$ | 42 | 78–79 | Ethyl acetate-hexane |
| 5 | 6,7-(CH$_3$)$_2$ | 4-Cl-phenyl | COOC$_2$H$_5$ | 70 | 170–171 | Ethyl acetate |

Note 1)
NMR (δ ppm in CDCl$_3$): 0.92(3H, t, J=7.2Hz), 4.06(2H, q, J=7.2Hz), 5.03(2H, s), 7.33–7.37(2H, m), 7.50–7.55(3H, m), 7.90–7.98(2H, m), 8.26(1H, d, J=9.4Hz)

TABLE 3

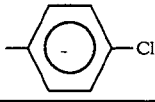

| Reference Example No. | $R^1$, $R^2$ | B | G | Yield (%) | Melting Point (°C.) | Recrystallization Solvent |
|---|---|---|---|---|---|---|
| 6 | 6,7-(OCH$_2$CH$_2$O) | 4-OCH$_3$-phenyl | COOC$_2$H$_5$ | 44 | 155–156 | Acetone-ether |
| 7 | 6,7-(CH$_3$O)$_2$ | phenyl | COOC$_2$H$_5$ | 23 | 153–155 | Acetone-ether |

TABLE 3-continued

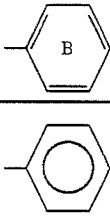

| Reference Example No. | R¹, R² | B | G | Yield (%) | Melting Point (°C.) | Recrystallization Solvent |
|---|---|---|---|---|---|---|
| 8 | 6,7-$(CH_3O)_2$ | 4-$OCH_3$-phenyl | $COOC_2H_5$ | 48 | 108–109 | Ether |
| 9 | 6,7-$(CH_3O)_2$ | 4-Cl-phenyl | $COOC_2H_5$ | 53 | 160–161 | Ethyl acetate-hexane |
| 10 | 6,7-$(CH_3O)_2$ | 4-$CH_3$-phenyl | $COOC_2H_5$ | 35 | 126–127 | Acetone-ether |
| 11 | 6,7-$(CH_3O)_2$ | 3,4-di-$OCH_3$-phenyl | $COOCH_3$ | 44 | 181–182 | Acetone-ether |
| 12 | 6,7-$(CH_3O)_2$ | 3,4-di-$OCH_3$-phenyl | $COOC_2H_5$ | 53 | 147–148 | Acetone-ether |

TABLE 4

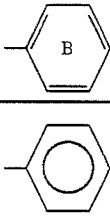

| Reference Example No. | A¹ | A² | B¹ | B² | Yield (%) | Melting Point (°C.) | Recrystallization Solvent |
|---|---|---|---|---|---|---|---|
| 26 | $CH_3O$ | $CH_3O$ | Cl | Cl | 57 | 159–160 | Ethyl acetate-hexane |
| 27 | $(CH_3)_2CHO$ | $CH_3O$ | $CH_3O$ | $CH_3O$ | 66 | 138–140 | Ethyl acetate-hexane |
| 28 | $CH_3O$ | $(CH_3)_2CHO$ | $CH_3O$ | $CH_3O$ | 48 | 125–126 | Ethyl acetate-hexane |
| 29 | $CH_3O$ | $CH_3O$ | $(CH_3)_2CHO$ | $CH_3O$ | 50 | 126–127 | Ethanol |
| 30 | $CH_3O$ | $CH_3O$ | $CH_3O$ | $(CH_3)_2CHO$ | 48 | 149–150 | Ethanol |
| 31 | $CH_3O$ | $CH_3O$ | $(CH_3)_2CHO$ | $(CH_3)_2CHO$ | 48 | 118–119 | Ethyl acetate-hexane |
| 32 | $CH_3O$ | $(CH_3)_2CHO$ | $(CH_3)_2CHO$ | $(CH_3)_2CHO$ | 60 | 99–100 | Ethyl acetate-hexane |

TABLE 5

[Structure: 4,5-dimethoxyphenyl ring with N=C(CH₂-NR)-Y=C(B)- substituent]

| Example No. | B | Y | -N(R) ring | Melting Point (°C.) | Recrystallization Solvent |
|---|---|---|---|---|---|
| 2 | 3,4-dimethoxyphenyl | C—COOC₂H₅ | imidazol-1-yl | 208–209 | Dichloromethane-hexane |
| 3 | 3,4-dimethoxyphenyl | C—COOC₂H₅ | 2-methylimidazol-1-yl | 177–178 | Ethyl acetate-hexane |
| 4 | 3,4-dimethoxyphenyl | C—COOC₂H₅ | pyrazol-1-yl | 134–135 | Ethanol |
| 5 | 4-methoxyphenyl | C—COOC₂H₅ | imidazol-1-yl | 200–201 | Ethyl acetate-hexane |
| 6 | 4-methoxyphenyl | C—COOC₂H₅ | 2-methylimidazol-1-yl | 148–149 | Ethyl acetate-hexane |
| 7 | 4-methoxyphenyl | C—COOC₂H₅ | pyrazol-1-yl | 157–158 | Ethanol |
| 8 | 3,4-dimethoxyphenyl | N | imidazol-1-yl | 184–185 | Dichloromethane-ethyl ether |
| 9 | 3,4-dimethoxyphenyl | N | 2-methylimidazol-1-yl | 223–224 | Dichloromethane-ethyl ether |

TABLE 6

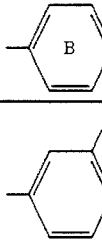

| Example No. | B | Y | -N-R | Melting Point (°C.) | Recrystallization Solvent |
|---|---|---|---|---|---|
| 10 | 3,4-(OCH$_3$)$_2$-phenyl | N | 2-ethyl-imidazol-1-yl | 188–189 | Ethyl acetate-hexane |
| 11 | 3,4-(OCH$_3$)$_2$-phenyl | N | pyrazol-1-yl | 198–199 | Dichloromethane-ethyl ether |
| 13 | 3,4-(OCH$_3$)$_2$-phenyl | C—COOC$_2$H$_5$ | 2-amino-imidazol-1-yl | 209–210 | Dichloromethane-hexane |
| 14 | 3,4-(OCH$_3$)$_2$-phenyl | C—COOC$_2$H$_5$ | 2-(N-methyl-acetamido)-imidazol-1-yl | 198–199 | Ethanol |
| 15 | 4-OCH$_3$-phenyl | C—COOC$_2$H$_5$ | 2-ethyl-imidazol-1-yl | 124–125 | Ethyl acetate-hexane |

TABLE 7

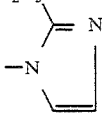

| Example No. | A$^1$ | A$^2$ | B$^1$ | B$^2$ | W | Yield (%) | Melting Point (°C.) | Recrystallization Solvent |
|---|---|---|---|---|---|---|---|---|
| 20 | CH$_3$O | CH$_3$O | H | Cl | CH | 65 | 156–157 | Ethyl acetate-hexane |
| 21 | CH$_3$O | CH$_3$O | Cl | Cl | CH | 64 | 183–184 | Ethyl acetate-hexane |
| 22 | CH$_3$O | CH$_3$O | Cl | Cl | N | 48 | 160–161 | Ethyl acetate-hexane |
| 23 | (CH$_3$)$_2$CHO | CH$_3$O | CH$_3$O | CH$_3$O | N | 58 | 154–155 | Ethyl acetate-hexane |
| 24 | CH$_3$O | (CH$_3$)$_2$CHO | CH$_3$O | CH$_3$O | N | 52 | —[1] | |

TABLE 7-continued

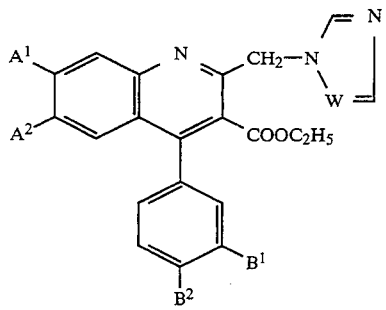

| Example No. | $A^1$ | $A^2$ | $B^1$ | $B^2$ | W | Yield (%) | Melting Point (°C.) | Recrystallization Solvent |
|---|---|---|---|---|---|---|---|---|
| 25 | $CH_3O$ | $CH_3O$ | $(CH_3)_2CHO$ | $CH_3O$ | N | 65 | 183–185 | Ethyl acetate-hexane |
| 26 | $CH_3O$ | $CH_3O$ | $CH_3O$ | $(CH_3)_2CHO$ | N | 75 | 165–166 | Ethyl acetate-hexane |
| 27 | $CH_3O$ | $CH_3O$ | $(CH_3)_2CHO$ | $(CH_3)_2CHO$ | N | 50 | 134–135 | |
| 28 | $CH_3O$ | $(CH_3)_2CHO$ | $(CH_3)_2CHO$ | $(CH_3)_2CHO$ | N | 66 | Oily substance[2] | |

[1]Amorphous solid. MNR (δ ppm in CDCl₃): 0.87(3H, t, J=7.2Hz), 1.33(6H, d J=6.0Hz), 3.85(3H, s), 3.93 (2H, q, J=7.2Hz), 3.96(3H, s), 4.02(3H, s), 4.43(1H, m), 5.68(1H, d, J=14.8Hz), 5.77(1H, d, J=14.8Hz), 6.82–7.01(4H, m), 7.41(1H, s), 7.93(1H, s), 8.27(1H, s)

[2]NMR (δ ppm in CDCl₃): 0.84(3H, t, J=7.2Hz), 1.26–1.45(18H, m), 3.93(2H, q, J=7.2Hz), 4.02(3H, s), 4.21(1H, m), 4.51(1H, m), 4.56(1H, m), 5.73(2H, s), 6.80–6.92(3H, m), 7.01(1H, d, J=8.2Hz), 7.41(1H, s), 7.93(1H, s), 8.27(1H, s)

TABLE 8

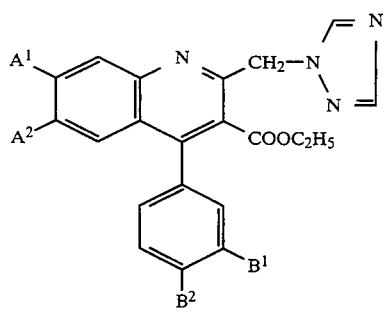

| Example No. | $A^1$ | $A^2$ | $B^1$ | $B^2$ | Yield (%) | Melting Point (°C.) | Recrystallization Solvent |
|---|---|---|---|---|---|---|---|
| 30 | HO | $CH_3O$ | $CH_3O$ | $CH_3O$ | 35 | 165–166[1] | |
| 31 | $CH_3O$ | HO | $CH_3O$ | $CH_3O$ | 38 | 215–216[2] | |
| 32 | $CH_3O$ | $CH_3O$ | HO | $CH_3O$ | 62 | 232–233 | Dichloromethane-hexane |

[1]NMR (δ ppm in CDCl₃): 0.88(3H, t, J=7.2Hz), 3.84(3H, s), 3.86(3H, s), 3.95(2H, q, J=7.2Hz), 3.97(3H, s), 5.73(2H, s), 6.88–7.01(5H, m), 7.52(1H, s), 7.94(1H, s), 8.37(1H, s)

[2]NMR (δ ppm in CDCl₃): 0.86(3H, t, J=7.0Hz), 3.85(3H, s), 3.94(2H, q, J=7.0Hz), 3.98(3H, s), 4.07(3H, s), 5.73(2H, s), 6.20(1H, broad), 6.82–6.98(3H, m), 7.08(1H, s), 7.42(1H, s), 7.93(1H, s), 8.27(1H, s)

TABLE 9

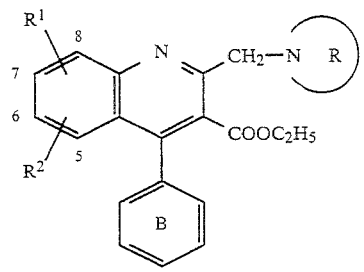

| Example No. | R¹, R² | B (ring) | -N⌒R | Yield (%) | Melting Point (°C.) | Recrystallization Solvent |
|---|---|---|---|---|---|---|
| 55 | 6-Cl, H | 4-Cl-phenyl | imidazol-1-yl | 34 | 112–114 | Ethanol |
| 56 | 6-CH₃, H | phenyl | imidazol-1-yl | 30 | 121–123 | Ethanol |
| 57 | 6-(CH₃)₂ | 4-Cl-phenyl | imidazol-1-yl | 40 | 133–135 | Ethanol |
| 58 | 6,7-(CH₃O)₂ | phenyl | imidazol-1-yl | 57 | 143–144 | Ethanol |
| 59 | 6,7-(CH₃O)₂ | 4-CH₃-phenyl | imidazol-1-yl | 43 | 139–141 | Ethyl acetate-hexane |
| 60 | 6,7-(OCH₂CH₂O) | 4-OCH₃-phenyl | imidazol-1-yl | 68 | 154–156 | Ethanol |
| 61 | 6,7-(CH₃O)₂ | 2,4-(OCH₃)₂-phenyl | indol-1-yl | 70 | 143–144 | Ethanol-hexane |
| 62 | 6,7-(CH₃O)₂ | 2,4-(OCH₃)₂-phenyl | 2-CHO-indol-1-yl | 75 | 160–161 | Dichloromethane-isopropylether |

What is claimed is:

1. A compound represented by the general formula:

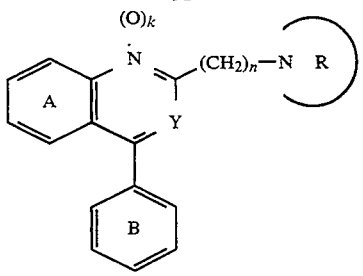

wherein Y represents a nitrogen atom or C—G, wherein G represents a carboxyl group which may be esterified; ring R is a nitrogen-containing unsaturated heterocyclic group which may be substituted or unsubstituted; each of rings A and B may have a substituent; n represents an integer from 1 to 4; and k represents the integer 0 or 1, or a salt thereof.

2. The compound of claim 1, wherein said nitrogen-containing unsaturated heterocyclic group is a 5-membered ring, or a salt thereof.

3. The compound of claim 1, wherein said nitrogen-containing unsaturated heterocyclic group contains 1 to 4 nitrogen atoms as ring component atoms, or a salt thereof.

4. The compound of claim 1, wherein said nitrogen containing unsaturated heterocyclic group is imidazol-1-yl, pyrazol-1-yl, 1,2,4-triazol-1-yl, 1,2,4-triazol-4-yl, 1,2,3-triazol-1-yl, pyrrol-1-yl or tetrazol-1-yl, or a salt thereof.

5. The compound of claim 1, wherein said n is 1, or a salt thereof.

6. The compound of claim 1, wherein said Y is C—G and G is a $C_{1-6}$ alkyloxycarbonyl group, or a salt thereof.

7. The compound of claim 1, wherein said G is an ethoxycarbonyl group, or a salt thereof.

8. The compound of claim 1, wherein each of A ring and B ring may independently be substituted with the same or different 1 to 4 substituents selected from the group consisting of a halogen atom, nitro, optionally substituted alkyl, optionally substituted hydroxyl, optionally substituted thiol, optionally substituted amino, optionally substituted acyl, optionally esterified carboxyl and an optionally substituted aromatic cyclic group, and the adjacent substituents may be linked together to form the group of the formula: —$(CH_2)_m$— or —O—$(CH_2)_l$—O— wherein m is an integer of 3 to 5 and l is an integer of 1 to 3 which forms a ring, or a salt thereof.

9. The compound of claim 8, wherein said optionally substituted hydroxyl group is methoxy group, or a salt thereof.

10. The compound of claim 8 wherein said optionally substituted hydroxyl group an unsubstituted hydroxyl group, or a salt thereof.

11. The compound of claim 1, wherein the substituent of the ring A is a methoxy group at the 6- or 7- position of the quinoline ring, or a salt thereof.

12. The compound of claim 1, wherein the substituent of the ring B is a methoxy group at the 3- or 4-position of the benzene ring, or a salt thereof.

13. The compound of claim 1 which is selected from the group consisting of:
6,7-dimethoxy-4-(3,4-dimethoxyphenyl)-2-(1,2,4-triazol-1-ylmethyl)quinoline-3-carboxylic acid ethyl ester, 6,7-dimethoxy-4-(3-isopropoxy-4-methoxyphenyl)-2-(1,2,4-triazol-1-ylmethyl)quinoline-3-carboxylic acid ethyl ester, 6,7-dimethoxy-4-(4-hydroxy-3-methoxyphenyl)-2-(1,2,4-triazol-1-ylmethyl)quinoline-3-carboxylic acid ethyl ester, 6,7-dimethoxy-4-(3,4-dimethoxyphenyl)-2-(2-ethylimidazol-1-ylmethyl)quinoline-3-carboxylic acid ethyl ester, 6,7-dimethoxy-4-(3,4-dimethoxyphenyl)-2-(pyrazol-1-ylmethyl) quinoline-3-carboxylic acid ethyl ester, 6,7-dimethoxy-4-(4-methoxyphenyl)-2-(1,2,4-triazol-1-ylmethyl)quinoline-3-carboxylic acid ethyl ester, 6,7-dimethoxy-4-(4-isopropoxy-3-methoxyphenyl)-2-(1,2,4-triazol-1-ylmethyl)quinoline-3-carboxylic acid ethyl ester, or a salt thereof.

14. An anti-inflammatory agent containing a compound represented by the general formula:

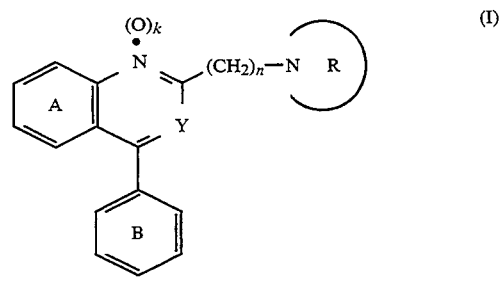

wherein Y represents a nitrogen atom or C—G, wherein G represents a carboxyl group which may be esterified; ring R is a nitrogen-containing unsaturated heterocyclic group which may be substituted or unsubstituted; each of rings A and B may have a substituent; n represents an integer from 1 to 4; and k represents the integer 0 or 1, or a salt thereof, along with a pharmaceutically acceptable carrier.

15. An anti-pyretic analgesic agent containing a compound represented by the general formula:

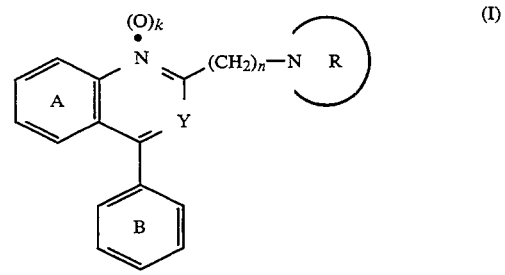

wherein Y represents a nitrogen atom or C—G, wherein G represents a carboxyl group which may be esterified; ring R is a nitrogen-containing unsaturated heterocyclic group which may be substituted or unsubstituted; each of rings A and B may have a substituent; n represents an integer from 1 to 4; and k represents the integer 0 or 1, or a salt thereof, along with a pharmaceutically acceptable carrier.

16. An anti-arthritic agent containing a compound represented by the general formula:

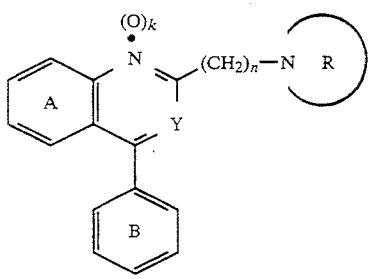

(I)

wherein Y represents a nitrogen atom or C—G, wherein G represents a carboxyl group which may be esterified; ring R is a nitrogen-containing unsaturated heterocyclic group which may be substituted or unsubstituted; each of rings A and B may have a substituent; n represents an integer from 1 to 4; and k represents the integer 0 or 1, or a salt thereof, along with a pharmaceutically acceptable carrier.

17. A method for the prophylaxis or treatment of inflammation in a mammal comprising administering an anti-inflammatory effective amount of an agent according to claim 14 to a mammal in need thereof.

18. A method for promoting antipyretic analgesic action in a mammal comprising administering an antipyretic analgesic effective amount of an agent according to claim 15 to a mammal in need thereof.

19. A method for the prophylaxis or treatment of arthritis in a mammal comprising administering an anti-arthritic effective amount of an agent according to claim 16 to a mammal in need thereof.

* * * * *